United States Patent [19]
Holen et al.

[11] Patent Number: 5,320,808
[45] Date of Patent: Jun. 14, 1994

[54] REACTION CARTRIDGE AND CAROUSEL FOR BIOLOGICAL SAMPLE ANALYZER

[75] Inventors: James T. Holen, Mundelein; Enrique Hicaro, Jr., Chicago; Caryn G. Putterman, Northbrook; Tung-Ming Huang, Elk Grove Village; Carl W. Merkh, Lindenhurst, all of Ill.

[73] Assignee: Abbott Laboratories, Abbott Park, Ill.

[21] Appl. No.: 227,590

[22] Filed: Aug. 2, 1988

[51] Int. Cl.⁵ .................... G01N 21/01; G01N 21/13
[52] U.S. Cl. .................... 422/64; 141/130; 141/163; 356/246; 422/58; 422/63; 422/68.1; 422/102; 422/104; 435/300; 435/301
[58] Field of Search .......... 422/56, 57, 58, 62, 422/63, 64, 65, 66, 68.1, 102, 104; 356/246, 426, 427; 435/300, 301; 141/130, 163

[56] References Cited

U.S. PATENT DOCUMENTS

| | | | |
|---|---|---|---|
| D. 287,633 | 6/1987 | Hollar et al. | 422/64 |
| 1,101,568 | 6/1914 | Roberts | 141/130 |
| 2,771,399 | 11/1956 | Savage | 422/58 X |
| 3,276,314 | 10/1966 | Robinson | 88/27 |
| 3,350,946 | 11/1967 | Isreeli | 73/423 |
| 3,425,568 | 2/1969 | Albright | 211/87 |
| 3,550,453 | 12/1970 | Lightner et al. | 73/422 |
| 3,680,967 | 1/1972 | Engelhardt | 356/246 |
| 3,785,773 | 1/1974 | Rohrbaugh | 23/253 |
| 3,857,491 | 12/1974 | Townsend et al. | 211/64 |
| 3,929,583 | 12/1975 | Sharpe et al. | 435/301 |
| 3,965,867 | 6/1976 | Berry | 23/253 R |
| 4,031,197 | 6/1977 | Marinkovich | 424/1 |
| 4,046,513 | 9/1977 | Johnson | 435/301 X |
| 4,126,418 | 11/1978 | Krasnow | 422/64 |
| 4,189,074 | 2/1980 | Davies | 224/42.06 |
| 4,322,216 | 3/1982 | Lillig et al. | 422/64 |
| 4,360,360 | 11/1982 | Chiknas | 422/64 |
| 4,371,498 | 2/1983 | Scordato et al. | 422/102 |
| 4,406,547 | 9/1983 | Aihara | 422/64 |
| 4,427,294 | 1/1984 | Nardo | 356/344 |
| 4,430,299 | 2/1984 | Horne | 422/64 |
| 4,431,307 | 2/1984 | Suovaniemi | 422/102 X |
| 4,459,360 | 7/1984 | Marinkovich | 436/513 |

(List continued on next page.)

FOREIGN PATENT DOCUMENTS

| | | |
|---|---|---|
| 0063810 | 11/1982 | European Pat. Off. . |
| 0287900 | 10/1988 | European Pat. Off. . |
| 2384023 | 10/1978 | France ................... 435/301 |

OTHER PUBLICATIONS

"*Allergen-Specific IgE Fast TM Test*", Derer et al., Application of the dot immunobinding assay to allergy diagnosis, J. Allergy Clin. Immunol., 74:85, 1984.

"*Allergy Screen*", Derer et al., Application of the dot immunobinding assay to allergy diagnosis, J. Allergy Clin. Immunol., 74:85, 1984.

Primary Examiner—James C. Housel
Assistant Examiner—A. Soderquist
Attorney, Agent, or Firm—Lawrence S. Pope

[57] ABSTRACT

A semi-automated biological sample analyzer and subsystems are provided to simultaneously perform a plurality of enzyme immuno assays for human IgE class antibodies specific to a panel of preselected allergens in each of a plurality of biological samples. A carousel is provided to position and hold a plurality of reaction cartridges. Each reaction cartridge includes a plurality of isolated test sites formed in a two dimensional array in a solid phase binding layer contained within a reaction well which is adapted to contain a biological sample to be assayed. The carousel and cartridges contain structures which cooperate to precisely position the cartridges in each of three separate dimensions so that each cartridge is positioned uniformly. An optical reader operating on a principle of diffuse reflectance is provided to read the results of the assays from each test site of each cartridge. Also provided is a subsystem which provides predetermined lot-specific assay calibration data which is useful for normalizing the results of various assays with respect to predetermined common standard values.

17 Claims, 11 Drawing Sheets

U.S. PATENT DOCUMENTS

| | | | |
|---|---|---|---|
| 4,476,149 | 10/1984 | Poppe et al. | 422/56 |
| 4,517,851 | 5/1985 | Tice | 422/64 |
| 4,567,149 | 1/1986 | Sell et al. | 422/68 |
| 4,591,570 | 5/1986 | Chang | 435/300 X |
| 4,615,360 | 10/1986 | Jacobs | 422/64 |
| 4,634,575 | 1/1987 | Kawakami et al. | 422/63 |
| 4,682,891 | 7/1987 | de Macario et al. | 422/102 X |
| 4,695,430 | 9/1987 | Coville et al. | 422/63 |
| 4,713,974 | 12/1987 | Stone | 422/64 X |
| 4,761,268 | 8/1988 | Andersen et al. | 422/63 |
| 4,803,154 | 2/1989 | Uo et al. | 435/301 X |
| 4,812,392 | 3/1989 | Miyake et al. | 422/65 |
| 4,814,282 | 3/1989 | Holen et al. | 422/72 |
| 4,829,010 | 5/1989 | Chang | 422/58 |
| 4,847,050 | 7/1989 | Jenkins et al. | 422/102 |
| 4,849,177 | 7/1989 | Jordan | 422/65 |
| 4,853,188 | 8/1989 | Toya | 422/64 |
| 4,900,513 | 2/1990 | Barker et al. | 422/63 |
| 4,919,894 | 4/1990 | Daniel | 422/102 |
| 4,933,147 | 6/1990 | Hollar et al. | 422/64 |
| 5,001,417 | 3/1991 | Pumphrey et al. | 422/64 X |

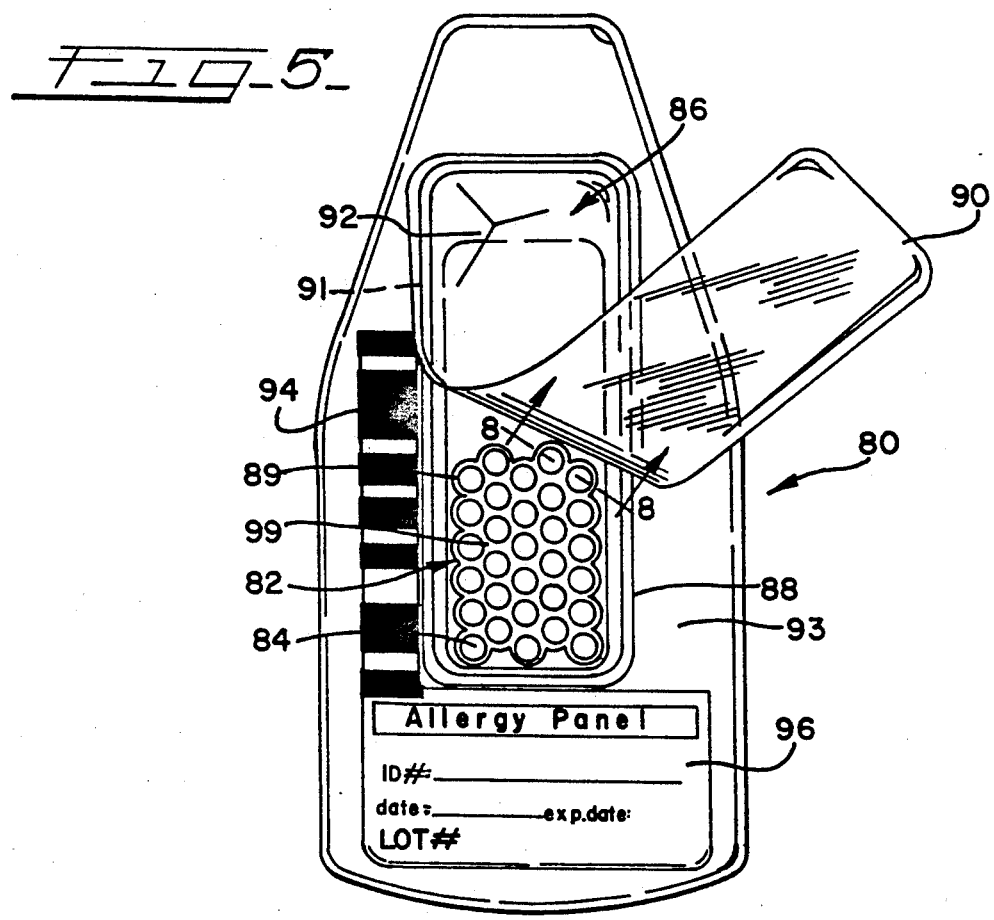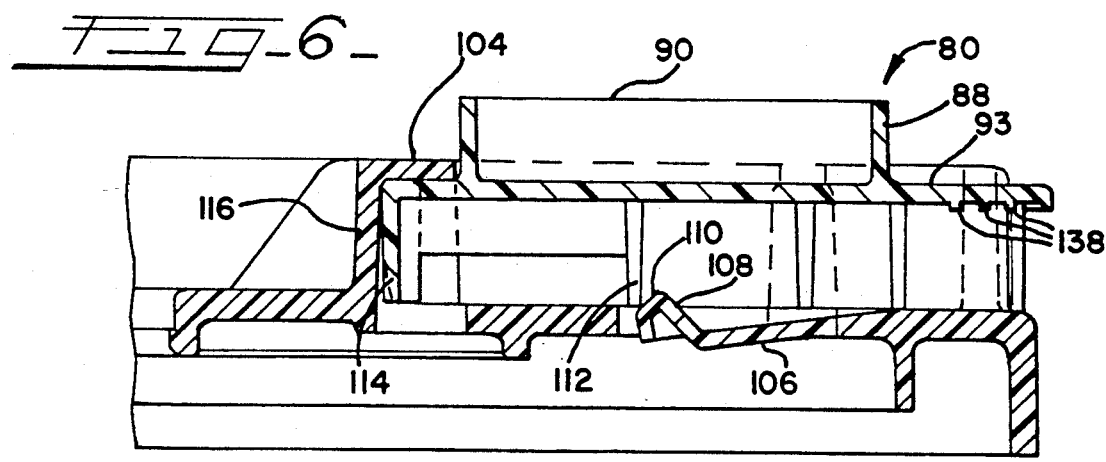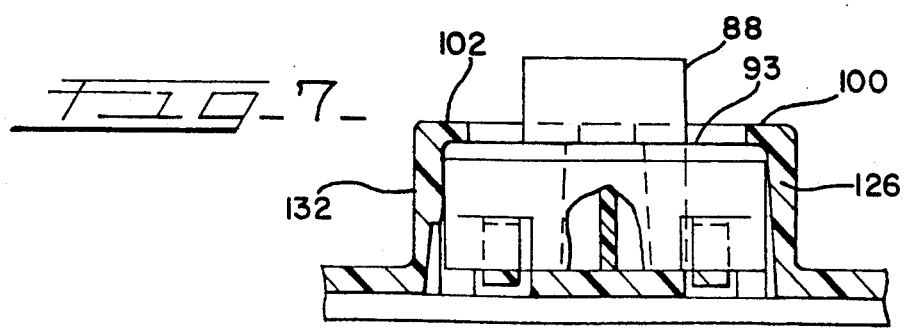

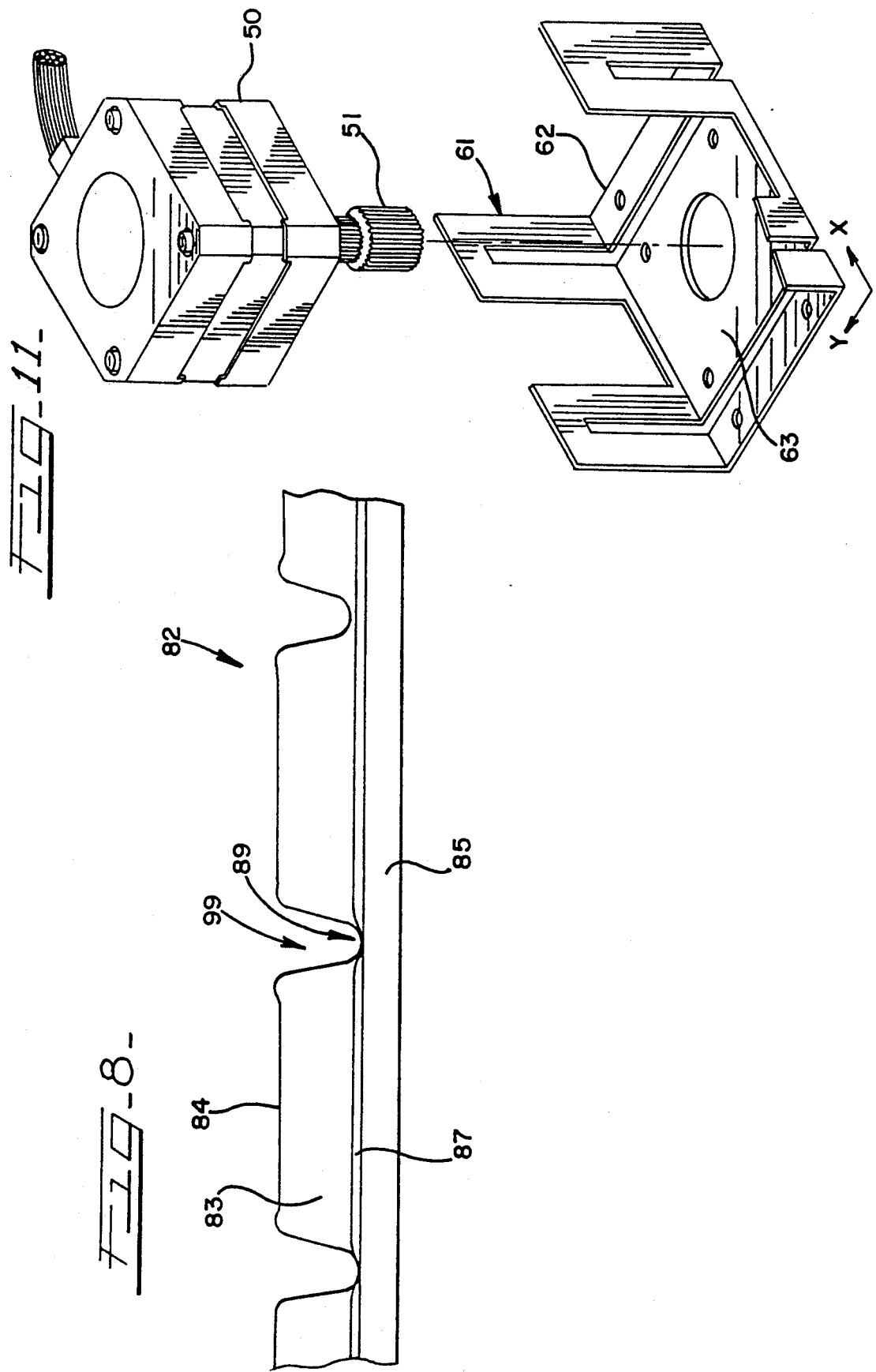

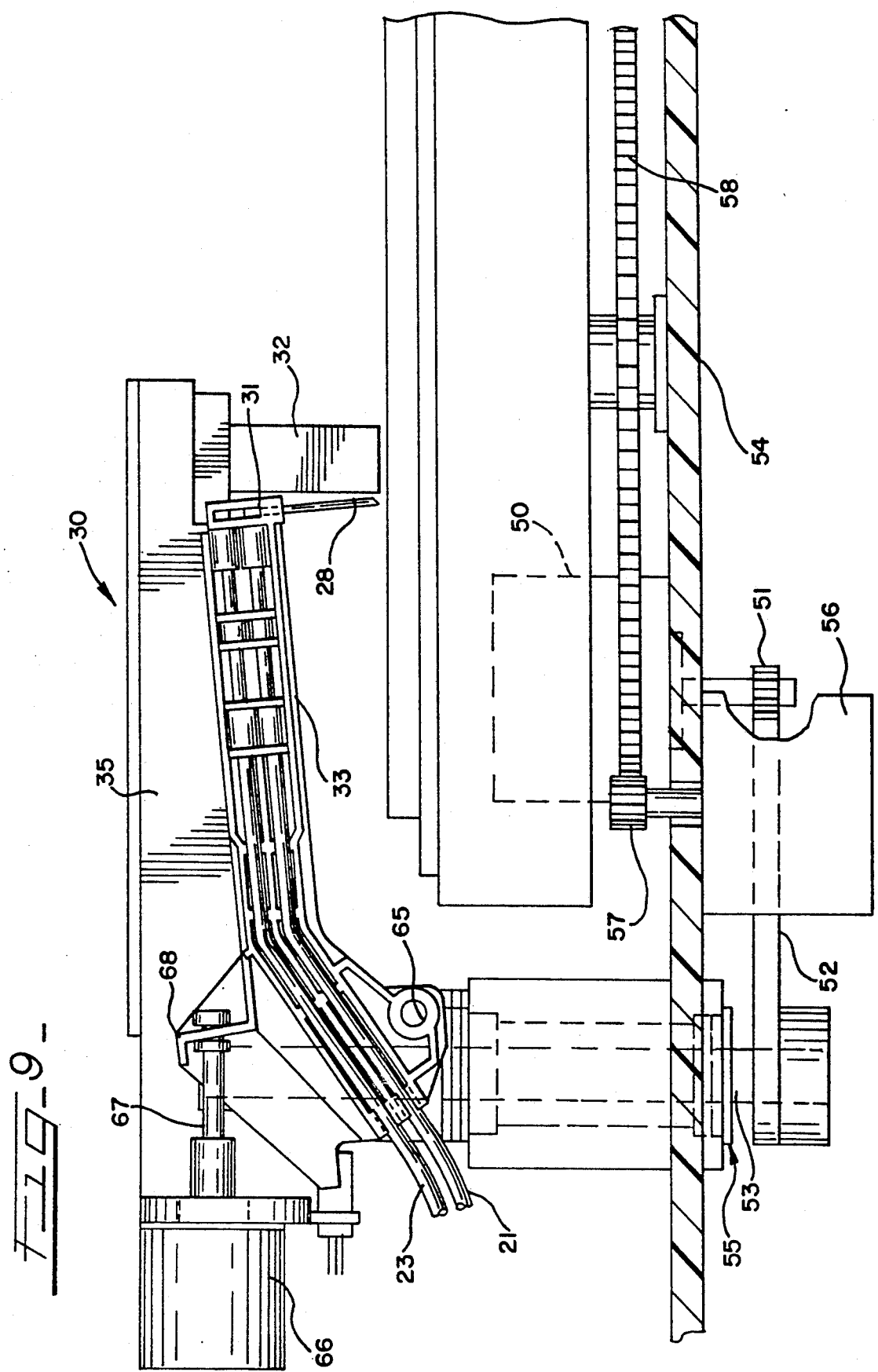

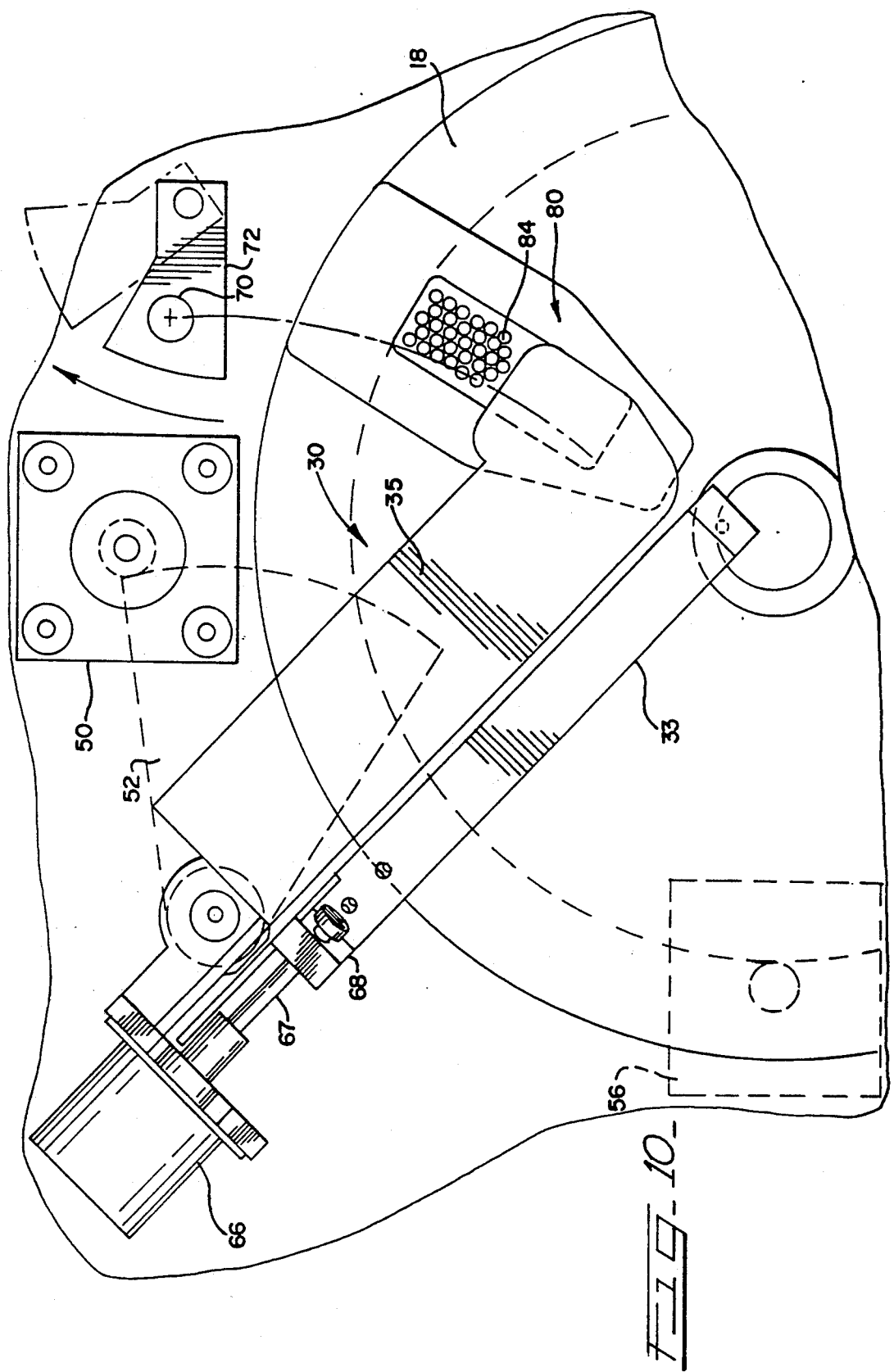

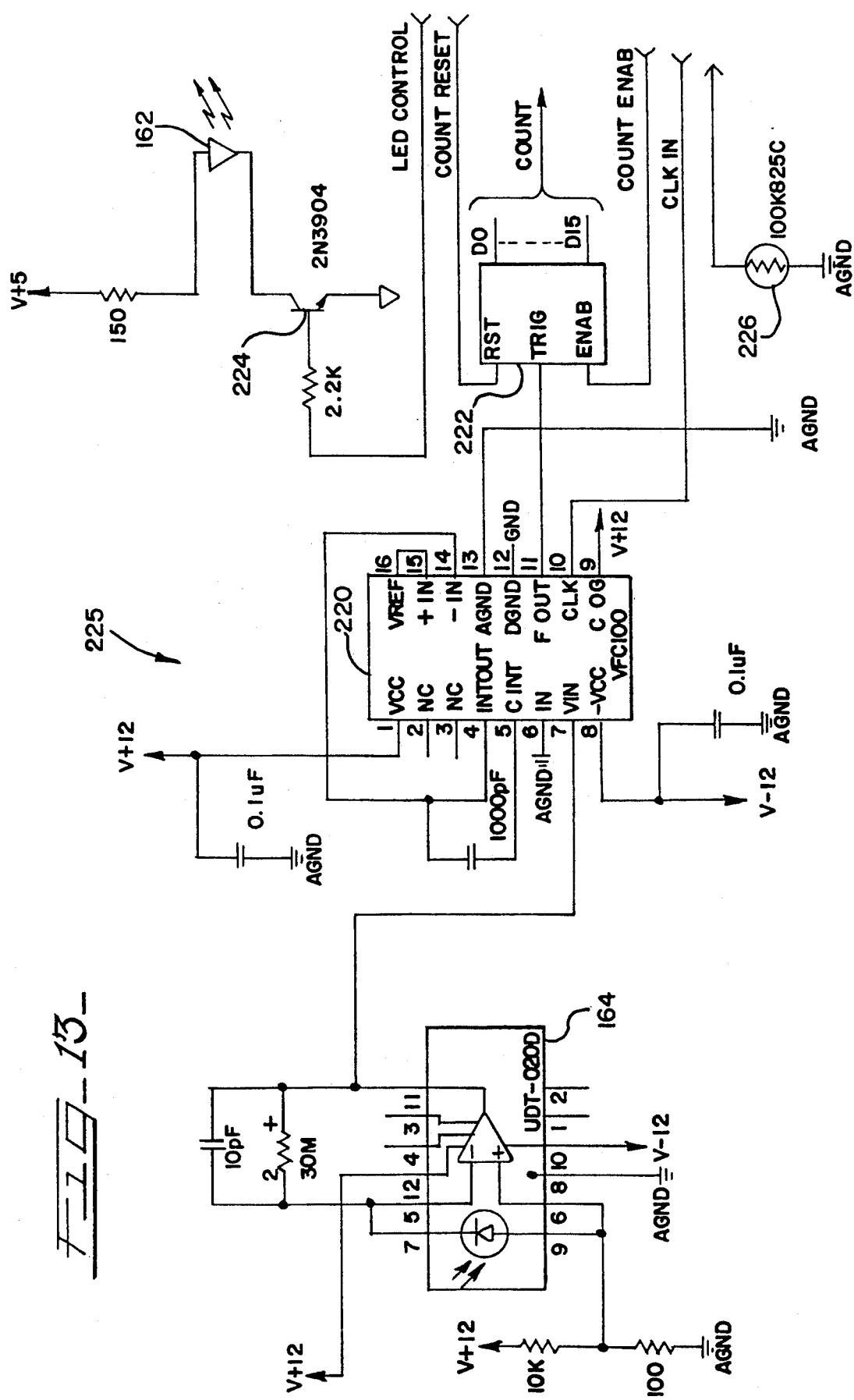
FIG-13-

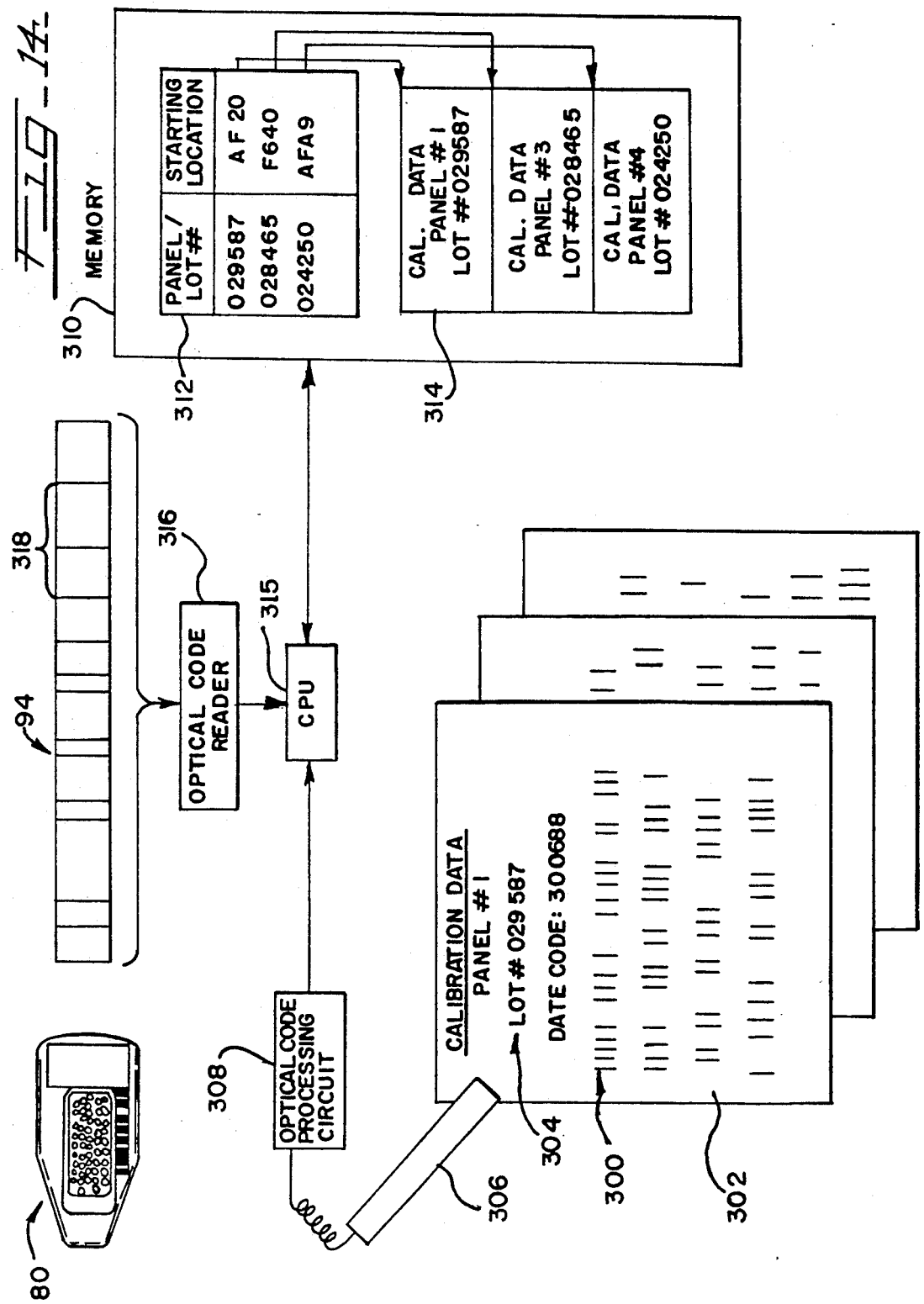

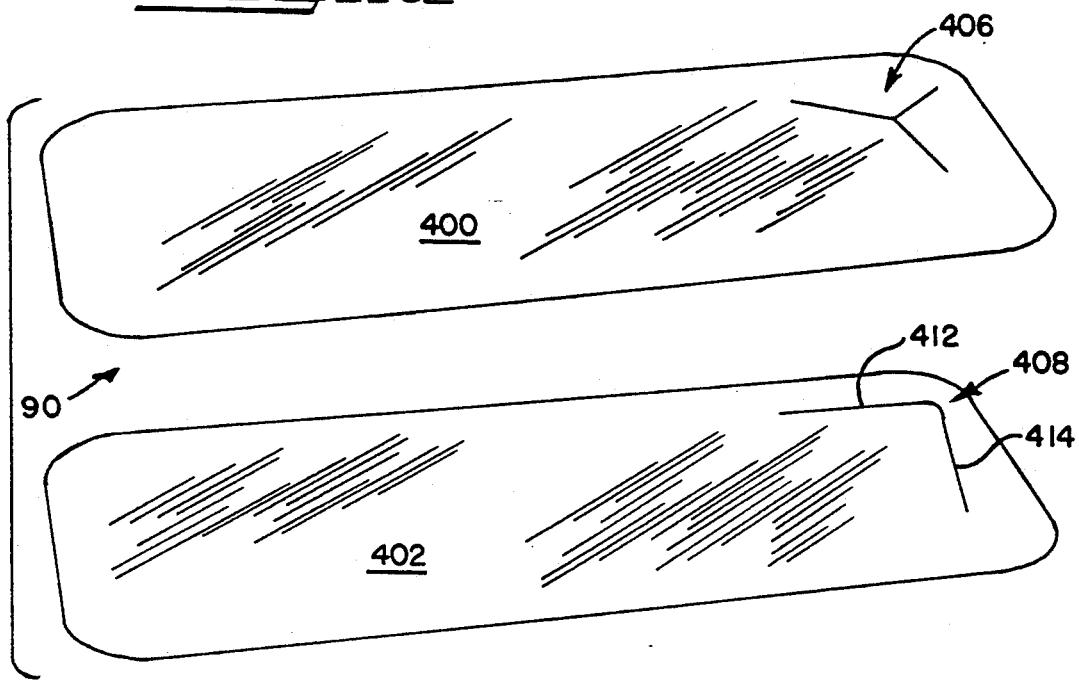
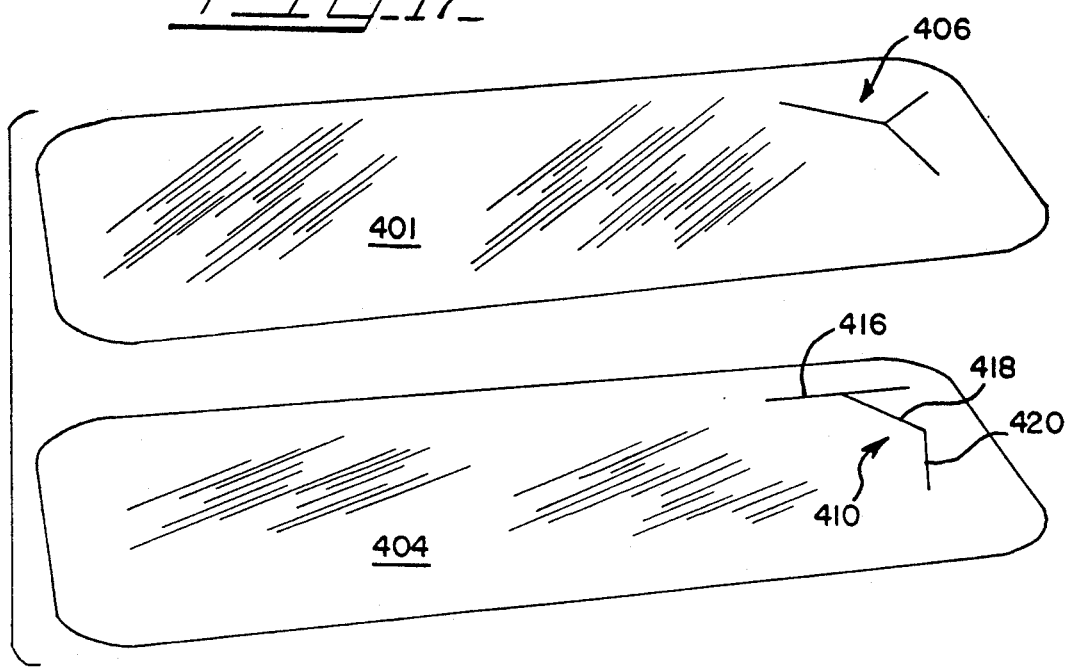

REACTION CARTRIDGE AND CAROUSEL FOR BIOLOGICAL SAMPLE ANALYZER

BACKGROUND OF THE INVENTION

The present invention relates generally to biological sample analyzers and more specifically to a semi-automated analyzer and subsystems thereof capable of simultaneously carrying out a panel of assays on each of a plurality of different biological samples. In one aspect, the analyzer of the invention is adapted to simultaneously assay each of a plurality of biological fluid samples for human IgE class antibodies specific to a preselected panel of allergens.

A significant portion of the population has some allergic reaction to substances such as pollen, animal dander, or other commonly present allergenic substances. A key element in the treatment of such allergic symptoms is identification of the particular substance to which a person may be allergic. Previous methods for determining allergic hypersensitivity were performed using direct skin tests on the patient. In these direct skin tests minute quantities of various allergens were injected into or under the patient's skin and the particular patch of skin was subsequently examined to determine whether or not a person had an allergic reaction to the previously introduced allergen.

In addition to being uncomfortable for the patient, patients on certain medications (i.e. antihistamines) cannot be accurately tested by direct skin tests.

Accordingly, a number of in-vitro testing procedures have been developed. Such procedures detect circulating IgE in serum or plasma or other microbiological interreactions using an insoluble solid carrier coated with a known quantity of antigan extract derived from a known allergenic substance. The coated carrier is typically exposed to, and incubated in, a sample of the patient's blood serum. If the patient carries the IgE class antibody which is specific to the particular allergen and which is the cause of the patient's allergic reaction to the allergen, a measurable binding reaction occurs on the carrier during the incubation period. The concentration of the IgE antibody in the sample and accordingly the degree of allergic sensitivity of the patient is then determined by measuring the magnitude of the binding reaction either visually, photometrically, fluorometrically, radiologically, enzymatically, or by other known techniques.

While such in-vitro procedures provide advantages over in-vivo testing procedures, they are not without disadvantages. First, a relatively large quantity of blood is required to test the patient's sensitivity to a large number of specific allergens. Second, testing for a large number of different allergens in separate cuvettes is tedious and -time consuming for the physician or technician performing the test.

To this end, efforts have been devoted to develop a system which simultaneously tests for a number of specific allergens utilizing a single sample of the patient's blood serum. For example, U.S. Pat. Nos. 3,941,876 (Marinkovich) and 4,031,197 (Marinkovich) disclose techniques for the screening of different IgE class antibodies. The techniques taught by Marinkovich involve coating an elongated cellulosic body, such as a strip of paper, with separate identified allergens to form bands or islands, which are separated from one another by allergen-free areas. The coated cellulose material is then contacted with a test serum so that serum IgE class antibodies specific for the coated allergens will bind to the appropriate bands or islands. The cellulosic body is then washed and subsequently incubated with labelled antibodies that are reactive with the attached IgE class antibodies. The bands or islands are then analyzed for the presence of the labeled antibodies.

U.S. Pat. No. 4,459,360 (Marinkovich) also discloses a similar multiple-component binding assay system which includes a plurality of coated filaments mounted on a support for simultaneously screening a liquid test sample for a plurality of components. Each of the filaments, which are preferably cotton threads, is used to bind a different allergen.

Another example of presently available invitro devices is given in U.S. Pat. No. 4,567,149 (Sell et al.), which discloses an apparatus including a well which contains a plurality of elongated strips. Each strip is coated with a separate assay binding component such as an antigen or allergen. The well is adapted to contain a liquid specimen for incubation with the strips. After the incubation process the liquid specimen is removed and the binding reaction which occurred on each strip is determined by known methods.

Still a further device which may be used for affecting a plurality of antibody-antigen reactions simultaneously in one operation is disclosed in European Patent Application No. 0 063 810 A1 (Gordon et al.). The Gordon reference teaches a device for carrying out immunoassays which comprises a solid porous support, preferably made of a nitrocellulose material, having antigens and/or immunoglobulins bound thereon by direct application, thereby forming an array of test areas. The array thus formed comprises a plurality of dots or lines of the antigen and/or immunoglobins.

Various systems are available which may be used in conjunction with the above-described multiple component binding assay systems to quantify the reactions which occur on the carriers. For example, U.S. Pat. No. 4,558,013 (Marinkovich et al.) discloses an apparatus (which may be used in conjunction with a device such as the one taught by Sell et al.) in which a carrier with an uncoated reference region is used to manually produce a strip of photographic film having a linear array of spots or stripes. Each spot or stripe on the film has an optical density indicating the magnitude of the binding reaction on a particular test strip or thread. A scanning densitometer is then used to successively measure the optical density of each film strip, thereby providing a quantitative measure of a patient's reaction to the various allergens.

Another device which may be used with the above-described multiple component binding assay systems to quantify the reaction of each specific allergen is taught in U.S. Pat. No. 4,510,393 (Sell et al.) which discloses a portable photo chamber which is used to manually photographically record the magnitude of a chemical reaction evidenced by the emission of radio-activity by a substrate labelled with a radioactive tracer.

Although these methods provide advantages over previously available in-vitro methods, and over the in-vivo methods, they are not without limitations. One major limitation is the fact that the methods for effecting and measuring the reactions on the above-described multiple test spot devices require an extensive amount of manual manipulation by the physician or technician performing the test, which increases the time, cost, and risk of error associated with such tests. For example, known in-vitro procedures require that the multicomponent biological test carriers be manually contacted with the liquid sample being analyzed, removed from the liquid sample, washed, and then incubated with a solution typically containing a labeled second antibody that is reactive with human IgE class antibodies. Subsequently the carrier must be manually removed from the solution and the magnitude of the resulting binding reaction on the solid phase be then determined by autoradiographical analysis in conjunction with densitometric analysis as proposed by Marinkovich, by fluorometry, or by other known techniques.

In addition, the washing step identified above normally comprises a multi-step procedure including removing waste fluid (for example used reagent or sample solution), adding wash solution, agitating the wash solution for a predetermined time period, removing used wash solution, adding more wash solution, and repeating the cycle two or more times before adding the next reagent. If a number of patient samples are to be analyzed simultaneously, the hands-on time requirements are further magnified. For instance, if often patient samples were to be analyzed, each washing step alone could involve performing 90 washes. This would probably require a minimum of approximately 30 minutes hands-on time for the technician or physician for each washing step required.

A number of analyzers for automatically analyzing a plurality of biological samples are known. Such analyzers typically include automated apparatus for providing wash, reagent, and sample fluids, and automated apparatus for measuring the results of the tests on the samples. See, for example, U.S. Pat. Nos. 4,427,294 (Nardo); 4,451,433 (Yamashita, et al.); 4,406,547 (Aihara); 4,634,575 (Kawakami, et al.); 3,964,867 (Berry); and 4,061,469 (DuBose).

Although these analyzers generally automate the analysis of a plurality of biological samples for the presence of a particular substance, none are suitable for carrying out the procedures required to simultaneously analyze a plurality of patient samples in a plurality of test cartridges each containing a plurality of different test sites and each adapted to simultaneously perform a complete panel of tests on a single sample.

Available systems have still further limitations. For instance, the accuracy of test results derived from devices such as those disclosed by Gordon et al. may be less than optimal. Since the test dots in the Gordon et al. device are formed by direct contact of the specific allergen with the nitrocellulose without an effective means for confining or isolating the allergen to a specific area, the accuracy and reliability of the results achieved with this device are affected. Specifically, if the dots are arranged in close proximity to each other there is a possibility that an allergen from one test dot will migrate onto a neighboring test dot when the allergen is applied to the support. This migration adversely affects the accuracy of the determination of the patient's reaction to the allergen associated with the neighboring test dot. Second, since the specific allergens are not confined to a predetermined area, the concentration of allergen will vary from dot to dot on each carrier and from carrier to carrier. As a result, depending on the detection technique employed, dot to dot variations in optical density or in the intensity of optical or other radiation resulting from the binding reactions on a dot will occur in dependence on the area over which the allergen initially dispersed during the initial contact with the support. Such variations have a substantial adverse affect on the uniformity and repeatability of test results.

Therefore, in view of the above, it is a general object of the present invention to provide a biological sample analyzer which may be used to automatically and simultaneously carry out a panel of tests on each of a plurality of patient samples.

It is a more specific object of the present invention to provide reaction cartridge means which are adapted for use in such an analyzer to simultaneously test a patient sample for a plurality of different components with a single addition of patient sample and selected reagents and which provides test results directly on the vector cartridge accessible by an optical reader.

It is also a more specific object of the present invention to provide reaction cartridge conveying means for such an analyzer including means to accurately and uniformly position a plurality of such cartridges in three separate dimensions so that an optical reader can accurately and uniformly read the results of a plurality of tests on each of a plurality of patient samples.

It is also a more specific object of the present invention to provide means adapted use with such an analyzer to provide access to a large volume of predetermined assay calibration data, such means preferably including reaction cartridge means provided with code means to access corresponding assay calibration data in a data storage means.

SUMMARY OF THE INVENTION

To achieve the foregoing and other objects and in accordance with the purposes of the present invention, automated apparatus for testing each of a plurality of biological samples for a plurality of selected assay binding components simultaneously is provided.

The apparatus includes reaction cartridge apparatus having a plurality of test sites each bound with a preselected first assay binding component which is adapted to capture a specific second assay binding component of interest in a biological sample.

Cartridge conveying apparatus or rack means having a plurality of mounting locations each adapted to hold a reaction cartridge is operative to selectively convey the reaction cartridges to positions at which selected biological samples and reagent fluids are introduced to the test sites on each cartridge to simultaneously carry out a preselected panel of tests on each sample. The cartridge conveying apparatus is further operative to selectively convey the reaction cartridges to a test result reading position.

Test result reader apparatus is provided to read the results of the tests directly from tile test sites on the cartridges at the reading position.

In one aspect of the invention, a reaction cartridge is provided which includes a plurality of isolated biological sample test sites contained within a reaction well which is adapted to contain a biological sample to be tested. The reaction well is configured to provide direct optical access to each of the test sites. The cartridge is further provided with lock means which cooperate with lock means on a cartridge-conveying carousel rack to position and lock the cartridge in three dimensions in a predetermined position on the rack. The rack preferably includes a plurality of openings each adapted to receive a cartridge.

In another aspect of the invention, apparatus is provided for providing assay calibration data adapted for use in assaying biological samples. Predetermined assay calibration data for normalizing the results of at least one assay with respect to at least one predetermined standard value includes a first code for identifying the at least one assay to which the calibration data corresponds. The calibration data is entered into a location in a data storage apparatus. Apparatus such as a reaction cartridge, which is adapted for use in carrying out at least one assay, includes a second code corresponding to the at least one assay. Apparatus responsive to the second code is provided for correlating the second code to the first code to access the calibration data in-the storage apparatus.

The foregoing objects, advantages and novel features of the invention as well as others will become apparent to those skilled in the art upon examination of the following detailed description of a presently preferred embodiment of the invention in conjunction with the appended drawings. The objects and advantages of the invention may be obtained by means of the instrumentalities and combinations particularly pointed out in the appended claims.

BRIEF DESCRIPTION OF THE DRAWINGS

FIG. 5 is an enlarged top plan view of a preferred embodiment of the reaction cartridge illustrated in FIG. 2.

FIG. 6 is a partial sectional view through lines 6—6 showing the cartridge mounted in the carousel illustrated in FIG. 3.

FIG. 7 is a partial sectional view through lines 7—7 showing the cartridge mounted in the carousel illustrated in FIG. 3.

FIG. 8 is a magnified view, partially cutaway, through lines 8—8 of FIG. 5 showing sample test sites in a preferred laminate structure of the test card of the present invention.

FIG. 9 is a cutaway side elevational view of a preferred embodiment of the boom arm and drive arrangements of the present invention.

FIG. 10 is a top plan view, partially in phantom, illustrating the range of motion of the preferred boom arm of the present invention.

FIG. 11 is an exploded perspective view, partially cutaway, of a preferred embodiment of a spring plate mounting arrangement for the boom arm and carousel drive motors of the present invention.

FIG. 13 is an electrical schematic diagram illustrating a preferred embodiment of a signal processing and control circuit for use with the optical reader of FIG. 12.

FIG. 14 is a block diagram illustrating a preferred embodiment of apparatus of the invention for providing assay calibration data for use in testing patient samples.

FIG. 16 is an exploded view of a preferred embodiment of the well cover comprising a part of the reaction cartridge of the present invention.

FIG. 17 is an alternate preferred embodiment of the well cover comprising a part of the reaction cartridge of the present invention.

DETAILED DESCRIPTION OF THE PRESENTLY PREFERRED EMBODIMENTS

Figure 1:
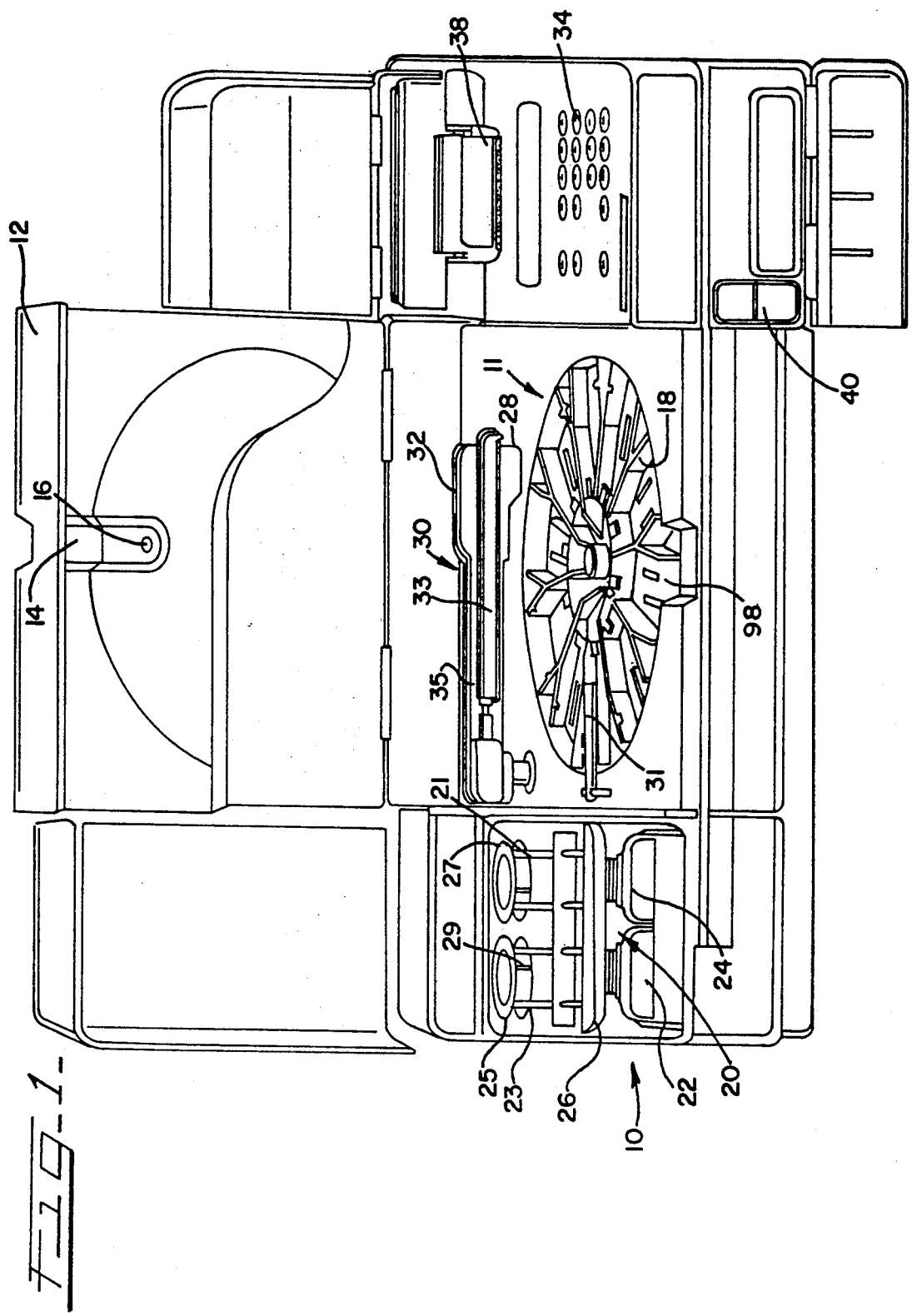
FIG. 1 is a perspective view of a preferred embodiment of the biological sample analyzer of the present invention.

Referring now to the drawings and specifically to FIGS. 1-10, a biological sample analyzer 10 includes a processing chamber 11 in which to test biological samples. A chamber door 12 is preferably hingedly mounted to the analyzer 10 overlying the chamber 11 to selectively close off and provide access thereto. Inset into the chamber door 12 is a translucent viewing window 14 which allows an operator to view the activity within the processing chamber. The window 14 preferably includes a reagent addition port 16 through which reagents can be introduced into the chamber 11 without opening the chamber door 12.

The processing chamber 11 contains a holding rack, preferably in the form of a rotatable carousel 18 which serves two primary purposes. First, the carousel 18 comprises means for holding and conveying reaction cartridges 80 in order to position the cartridges to receive sample and selected reagents, to provide agitation required for processing the samples and reagents, and to position the cartridges for reading test results therefrom. Second, the carousel 18 functions as a very precise optical bench, accurately positioning each reaction cartridge 80 relative to an optical reader 32, which is described in detail below, to facilitate accurate and repeatable reading of test results directly from the cartridges 80. Positioning and alignment of the cartridges 80 is preferably accomplished using a three-point system associated with each cartridge 80. The three-point alignment system is more fully described below. The carousel 18 also preferably includes optical positioning means which is used to provide precise alignment of the carousel and the optical reader 32 in a manner described in detail below.

As illustrated in FIG. 1, the carousel 18 is preferably disposed on a tilted axis. Rotation of the carousel 18 about this tilted axis provides desirable agitation of the fluids in a reaction well 86 of each reaction cartridge 80 thereby promoting faster and more complete reactions and allowing the use of smaller volumes of sample and reagents than has previously been possible. Rotation is preferably accomplished at a speed less than 25 rpm to avoid the effects of centrifugal force. Applicants have successfully used rotational speeds in a range between 7 to about 20 rpm. The carousel 18 is preferably tilted such that when a reaction cartridge 80 is at the rear of the analyzer 10, the reaction cartridge 80 is at the top of the tilt, thereby forcing fluid to collect at one end of the reaction well 86 (towards the top of the reaction cartridge as shown in FIG. 5). As the carousel 18 rotates, fluid in the reaction well 86 flows across the surface of a test card or panel 82 toward the other end of the reaction well until the reaction cartridge 80 reaches the bottom of the tilt (adjacent to the front of the analyzer). The fluid motion is then repeated in the opposite direction as the carousel 18 continues to rotate the reaction cartridge 80 back toward the top of the tilt, thereby providing desirable fluid agitation.

The tilt of the carousel 18 may be implemented by any conventional support structure, but preferably is implemented by mounting the carousel 18 on a base, which is inclined at the desired angle by conventional support means. A tilt angle of approximately 10° is presently preferred but, as will be recognized by those skilled in the art, the tilt may be within any appropriate range, for example 5–20°, which provides the desired agitation.

As described above, in manual testing procedures, washing of reaction supports or containers is by far the most tedious chore for the person performing the test. The presently preferred biological sample analyzer 10 of the present invention eliminates these tedious operator steps by automating the washing function using the combination of a microprocessor-controlled wash/waste unit 20 and the tilted carousel 18.

The wash/waste unit preferably comprises a dual chamber container which includes a chamber 22 for holding wash solution, and a chamber 24 which provides containment for waste fluid aspirated from the reaction cartridges 80. A wash manifold 26 functions both as a cover for the chambers and as a mount for wash tubing 23 and waste tubing 21. The cover 26 is preferably provided with suitable sealing means to prevent evaporation of the fluids contained in the wash and waste chambers 22 and 24.

In a preferred embodiment, a liquid level sensor (not shown) may be associated with the waste chamber 24 to detect when the waste chamber 24 is full and provide a detection signal. An optical sensor (not shown) may also be provided to generate a detection signal when the cover 26 is not in an appropriate position (such as when the cover and/or the container wash/waste container are removed).

Wash and waste fluids are caused to flow through wash and waste tubing 23 and 21 by means of peristaltic pumps 25 and 27. The first peristaltic pump 25 is operative to deliver wash solution from the chamber 22 through tubing 23 while the second pump 27 is operative to aspirate waste fluids through the tubing 21 and into the waste chamber 24. For reasons which will become apparent, the waste pump 27 is preferably operated to generate a higher flow rate than the wash pump 25. Thus, the pin 29 of the wash pump 25 is disposed at a radius less than the radius of the pin of the waste pump 27. The selection, construction, and operation of suitable peristaltic pumps is well known to persons skilled in the art and a detailed description is not necessary to a complete understanding of the invention.

Wash and waste fluids are preferably introduced into and removed from the reaction wells 86 of reaction cartridges 80 mounted on carousel 18 by means of a fluid probe 28 which is connected with the wash and waste tubing 23 and 21 and which is mounted proximate the free end of a horizontal, pivotally-mounted probe arm 33. In a preferred embodiment, fluid access to a reaction cartridge 80 is provided when the carousel 18 conveys the reaction cartridge 80 to a preselected wash position (preferably around the one o'clock position on the carousel 18 as viewed from the front of the biological analyzer 10 in FIG. 1). At this position, the tilt of the carousel 18 causes any fluid in the reaction well 86 to gravitate towards a corner of the reaction well 86. The probe arm 33 is rotated so that the fluid probe 28 is positioned above the reaction well 86 of the reaction cartridge 80. The probe arm 33 then pivots downwardly, causing the probe 28 to dip down into the corner of the reaction well. Pump 27 or 25 is then operated to either aspirate fluid from or introduce fluid into the reaction well 86.

Details of the assay protocol are discussed hereinafter. Upon completion of a panel of tests, the test results are preferably read by an optical reader system which is more fully described below, but which generally includes an optical reader 32 and an associated control and signal processing circuit. Briefly, the optical reader 32 includes a source of optical radiation, an optical detector, and an array of lenses, apertures and filters. The optical reader 32 is preferably mounted in a reader head which is in turn disposed proximate the free end of a horizontal rotatably-mounted optical reader arm 35. In order to read a test result from a test site 84 on a reaction cartridge, the reaction cartridge 80 is conveyed by the carousel 18 to a predetermined reading position. The reader arm 35 is then rotated out over the reaction well 86 of the reaction cartridge 80 until the test site 84 to be read is aligned directly under the optical reader 32. The optical source of the optical reader 32 then emits a beam of optical radiation onto a small portion of the test site 84 and the optical detector converts the intensity of the optical radiation reflected by the diffuse surface of the test site into an electrical signal. The signal is then processed to obtain the optical density value of the test site 84 which is directly related to the concentration of a binding component of interest in the biological sample which is specifically reactive with the capture reagent or binding component disposed on the test site. Under microprocessor control, the carousel 18 and optical reader arm 35 move in cooperation to sequentially position the optical reader 32 over each selected test site 84 until all selected test sites 84 have been read.

As shown in FIG. 1, the biological sample analyzer 10 preferably also includes a keyboard 34, which may be used by an operator to enter data and instrument function commands. The analyzer also preferably includes a conventional display 36 and printer 38 which may be used to prompt the operator to take action during a test cycle and to provide a record of test results.

The keyboard 34 preferably includes numeric keys that allow the user to enter data such as assay calibration data or the patient I.D. number associated with a certain reaction cartridge 80. The keyboard 34 also preferably includes instrument function keys including for example an ENTER key which is operative to enter data from the keyboard, a RUN key which is operative to initiate or resume a test procedure and an INDEX key which is operative to rotatably advance the carousel 18 by one position. Other keys which allow keyboard data to be cleared or which provide control commands for the printer (such as to eject paper or to pause the test operation) may also be provided.

As mentioned above, a controlled test environment is preferably provided in the processing chamber 11. During an exemplary enzyme immuno assay which is described in detail below for example, the temperature in the chamber is preferably maintained at approximately 35° C. Temperature in the processing chamber 11 is suitably maintained at a selected level by means of one or more conventional electric coil heaters, fans, temperature sensors, and a temperature control circuit in a manner well known to persons skilled in the art. Most simply, for example, the control circuit would operate to compare the analog voltage across the thermistor with an analog reference voltage corresponding to the desired temperature. If the thermistor voltage were below the reference voltage, the control signal would issue a signal to turn on the heater. The fan would operate to continuously circulate air in the processing chamber 11. In a more preferred embodiment, however, a microprocessor may read the temperature from the temperature sensors at predetermined intervals and control the heater to maintain the temperature at the desired level.

The locations of the various temperature control components are not critical. However, it is preferable that any fans be mounted or the air from the fans be directed in such a way as to avoid directly circulating across the optics reader 32 and optical reference means 70 which are described in detail below in order to minimize depositing debris which may affect the optical measurements of test results. The selection, construction and operation of the various temperature control components are well known to persons skilled in the art and further detailed explanation thereof is not necessary for a complete understanding of the invention.

In addition to the temperature control components described above a conventional electrical resistance type heating strip 31 may be provided in the reaction chamber 11 proximate to and overlying the rotational path of the carousel 18 to apply additional heat to reaction cartridges 80 as they are rotated on the carousel 18. Use of such a heating strip 31 is particularly advantageous in preventing condensation from forming on the well covers 90 of the reaction cartridges 86 which condensate can affect the concentration of fluids in the reaction wells 86, adversely affect test results, and constitutes a biohazard.

In a particularly preferred embodiment, the biological sample analyzer 10 also includes optical code reader means 306 which may be a conventional optical bar code reader wand and associated processing circuitry 308 (illustrated in FIG. 14). As described in detail below, the optical code reader means 306 is used to particular advantage to enter large amounts of assay calibration data into the biological sample analyzer 10, which data is then used in the preferred embodiment to normalize the test results obtained from various test sites 84 on various reaction cartridges 80. If desired, a storage compartment 40 can be provided to store the optical code reader means 306 when not in use.

CAROUSEL AND REACTION CARTRIDGES

Referring now to FIGS. 1–7, a more detailed description is given of the reaction cartridges 80 and the carousel 18. As best illustrated in FIG. 5, the preferred reaction cartridge 80 includes a test card 82 which includes an array of test sites 84 preferably in close proximity to each other. The test card 82 is contained within a reaction well 86 which is defined by a well wall 88. The reaction well 86 is preferably provided with a removable, preferably transparent well cover 90 which preferably includes a reagent port 92 to facilitate the delivery and removal of fluids from the reaction well 86.

The well cover 90 is preferably made of one or more layers of a thin transparent material with fairly resilient properties, such as a polyester film. A suitable polyester film is commercially available as MYLAR. The port 92 preferably is defined by multiple slits in the well cover 90. The slits are preferably disposed in one of the lower corners of the reaction well 86 and arranged to define a generally Y-shaped port. Since the cover 90 is made of a fairly resilient material this arrangement provides a self-sealing port. The cover 90 is preferably removably adhered to the top of the well wall 88 using a suitable adhesive.

As described in more detail below, to further enhance the sealing capabilities of the port 92 of the cover 90, the port 92 preferably includes a second flap system formed in a second layer of polyester film and attached to the underside of the first layer of polyester film of the cover 90.

A first preferred embodiment of the dual layered cover including the second flap system is illustrated in FIG. 16. The cover 90 includes a first layer 400 bonded to a second layer 402 by a suitable adhesive. The first layer 400 includes three slits which intersect at a single point and are configured in a generally Y-shaped arrangement. The Y-shaped slit arrangement defines a first layer port 406 with a first hinged flap arrangement. The second layer 402 includes a pair of slits 412, 414 configured in a generally V-shaped arranged which define a second layer port 408 with a second layer hinged flap arrangement. As illustrated in FIG. 16, the first layer flap arrangement and the second layer flap arrangement are disposed such that the slits of each port 404, 408 do not directly line up. In this manner the flap of the second layer 402 seals the slits of the port 406 in the first layer 400. The flap areas of both layers contain minimal or no effective adhesive to insure free operation.

FIG. 17 illustrates another preferred embodiment of a dual layered cover 90 including a second flap system. The first or top layer 401 has a Y-shaped port 43 configuration similar to the port 406 of the first layer 400 of the embodiment illustrated in FIG. 16 and discussed above. The second layer 404 includes slits 416, 418 and 420. The slits 416 and 418 are disposed such that they define a generally Y-shaped slit arrangement. The slits 418 and 420 are disposed such that the two slits 418 and 420 define a generally V-shaped arrangement. The three slits 416, 418 and 420 define a second layer port 410 with a second layer flap arrangement. As with the embodiment illustrated in FIG. 16, the flap arrangement of port 403 and the flap arrangement of the port 410 are disposed such that the slits of each port 403, 410 do not directly line up.

With the preferred embodiments of the port 92 illustrated in FIGS. 16 and 17, when the probe or syringe needle, for example, enters the reaction well 86 through the slits at the Y-shaped port in the first or top layer, the hinged flap in the bottom or second layer is pushed down, thereby opening the port 92. When the probe 28 or needle is withdrawn, the hinged flap returns to its normal position, sealing the slits of the port 92 and thereby further enhancing the sealing capabilities of the port 92.

The reaction cartridge 80 also preferably includes code means 94 such as an optical bar code which is attached to or printed directly on the flat surface 91 of the reaction cartridge 80. The bar code 94 is adapted to be read by the optical reader 32 or by other conventional optical reader means. In a particularly preferred embodiment, the bar code 94 includes a lot code which is advantageously used to access stored assay calibration data corresponding to the particular reaction cartridge 80 being tested. A more detailed description of this feature of the invention is given below.

The reaction cartridge 80 also preferably includes a panel 96 which may include information such as the expiration date of the particular reaction cartridge, the lot number of the particular panel of the capture reagents or assay binding components used to manufacture the reaction cartridge, and a section on which the operator may manually record information such as a patient I.D. number and/or the date of the sample being tested.

Figure 2:
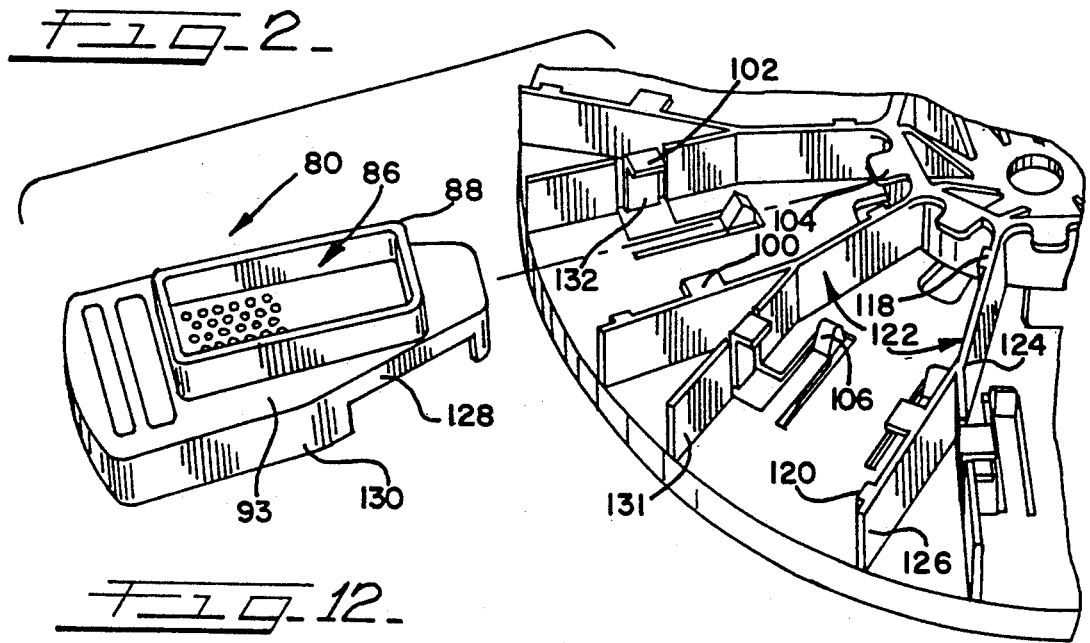
FIG. 2 is a perspective view of a preferred embodiment of a reaction cartridge and a partial cutaway view of a preferred cartridge-conveying carousel of the present invention.
Figure 3:
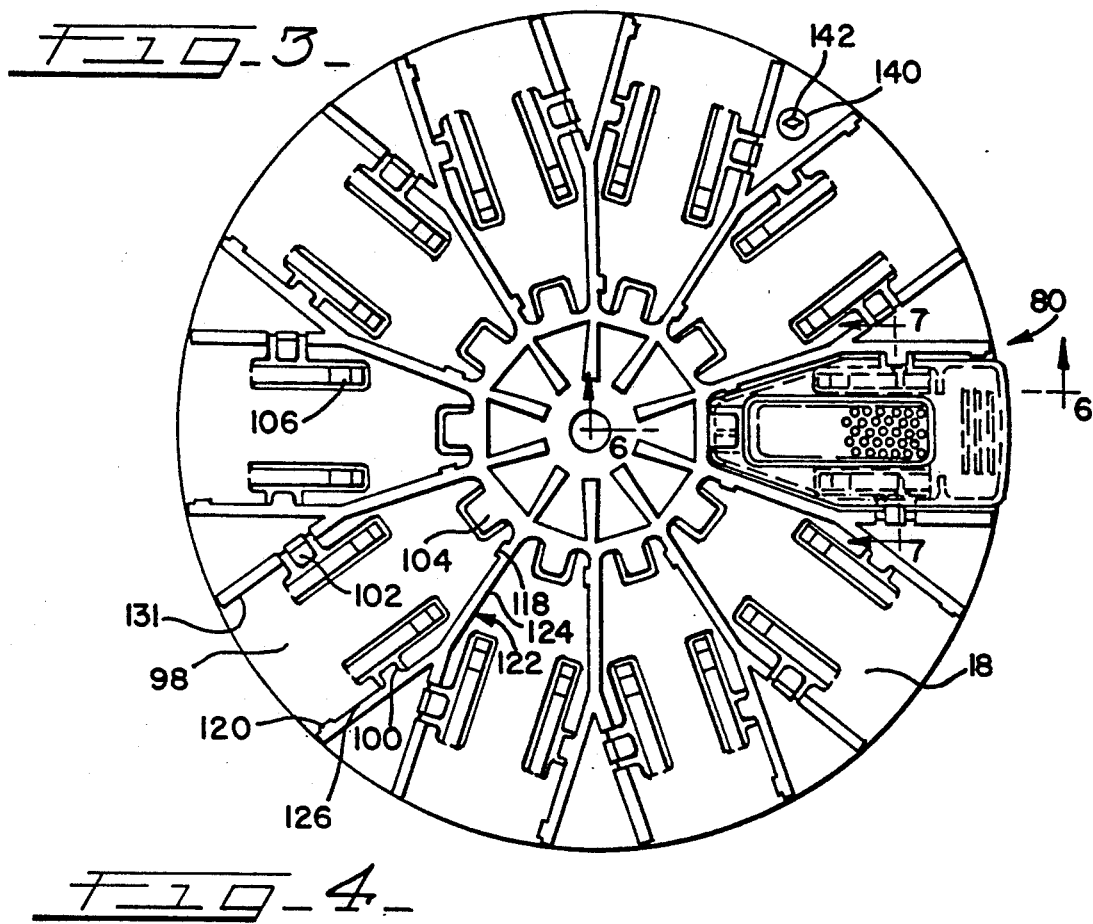
FIG. 3 is a top plan view of a preferred embodiment of the carousel of FIG. 2 illustrating the preferred cartridge positioning means of the present invention.
Figure 4:
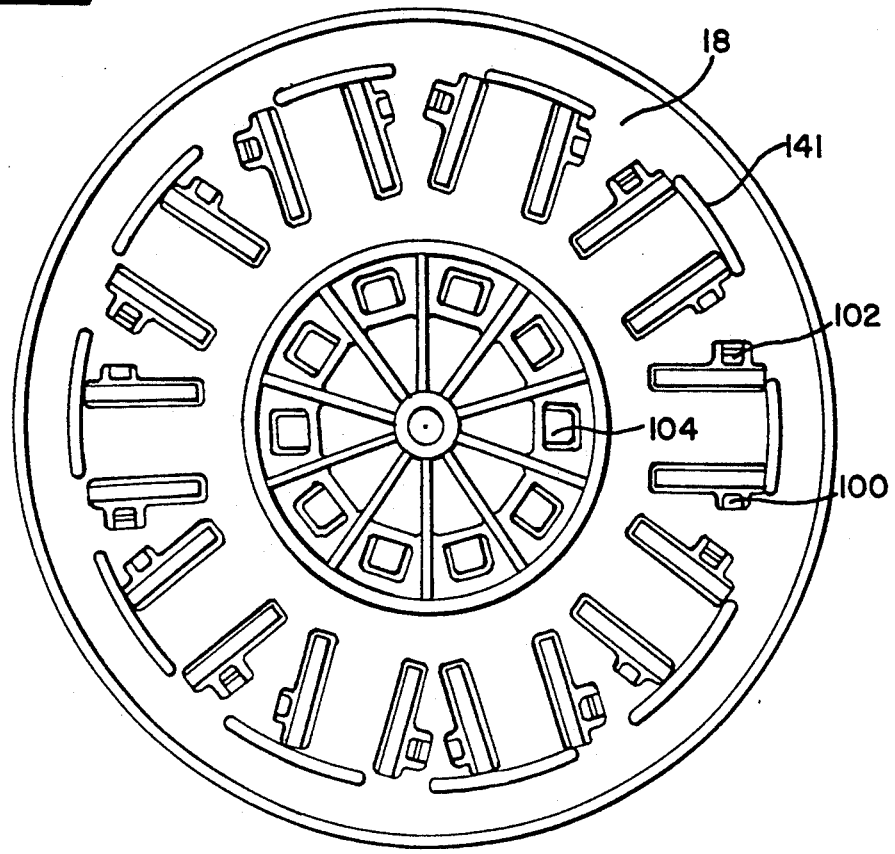
FIG. 4 is a bottom plan view of the carousel of FIG. 3.

Referring now specifically to FIGS. 2-4, the carousel 18 includes a plurality of openings 98 which are adapted to receive the reaction cartridges 80. Lock means are provided on the carousel 18 and the reaction cartridges 80 which cooperate to precisely position and lock each reaction cartridge 80 in the opening 98 in a precise predetermined position. Such positioning is preferred in order to minimize variations in the positioning of the cartridges relative to the optical reader 32 and the attendant position-induced variations in the readings of the test results from cartridge to cartridge.

Preferably, a three-point system is used to position and lock each cartridge 80 in an opening 98. The three-point locking system includes means for positioning and locking the reaction cartridge 80 in each of three predetermined dimensions, i.e., in a radial direction, a circumferential direction, and a vertical direction. A radial direction is defined here as a direction which extends radially from the center of the carousel 18 and a circumferential direction is defined here as a direction around the circumference of an imaginary circle which is concentric with the carousel 18.

Preferably the means for positioning a cartridge 80 in the vertical direction includes a set of tabs 100, 102 and 104 which are mounted at predetermined vertical distances above the surface of the carousel 18 and which are adapted to engage the top of the flat horizontal surface 93 of the reaction cartridge 80. The positioning means preferably further includes means for vertically biasing the reaction cartridge 80 such that the surface 93 firmly engages the tabs 100, 102 and 104.

The preferred vertical biasing means includes spring clips 106 which are preferably integrally formed in the surface of the carousel 18 by molding or another suitable process of manufacture. The spring clips 106 preferably include a first angled face 108 and a second angled face 110. The first angled face 108 is adapted to engage a vertically extending transverse rib 112 on the bottom of the reaction cartridge 80 as the reaction cartridge 80 is inserted radially into the opening 98 and to urge the spring clip 106 downwardly to allow entry of the cartridge. The second angled face 110, which is preferably oppositely inclined to the first angled face 108, is adapted to engage the rib 112 of the reaction cartridge 80 after it passes over the face 108 to lock the cartridge 80 in position. The angled face 110 biases the rib 112 and thus the cartridge 80 upwardly such that the flat horizontal surface 93 firmly engages the tabs 100, 102 and 104. The angled face 110 also functions to lock the reaction cartridge 80 in the predetermined vertical position.

Preferably, the ribs 112 are made of the same material as the base of the reaction cartridge 80 and are formed as an integral component thereof, for example by a conventional plastic molding process. In addition to ribs 112, as best illustrated in FIG. 6, the preferred reaction cartridge 80 also includes a flat substantially-vertical wall 114 at the front of the cartridge 80. The vertical wall 114 is adapted to engage a substantially-vertical mating wall portion 116 on the carousel 18. The carousel wall portion 116 is preferably arranged as a circumferentially extending wall portion as best seen in FIGS. 2 and 3. The mating walls 114 and 116 preferably include at least one contact point tangential to the circumferentially extending wall portion 116. The angled faces 110 of the spring clips 106 function to urge or bias the cartridge 80 in a forward or inward radial direction such that the mating walls 114 and 116 firmly engage at the contact point and the cartridge 80 is locked in a precise predetermined radial position.

The means for positioning a cartridge 80 in a circumferential direction preferably includes at least one and preferably a plurality of circumferential contact points between the carousel 18 and the reaction cartridge 80 and means for circumferentially biasing the cartridge 80 to firmly engage the carousel 18 at these circumferential contact points. In a preferred embodiment, the carousel 18 includes vertical walls 122 which are preferably formed as an integral component of the carousel 18, for example by a conventional plastic molding process. The vertical wall 122 includes a radially-extending portion 124 which includes a first circumferential contact point 118 and an angled portion 126 which includes a second circumferential contact point 120. The preferred reaction cartridge 80 includes a wall which is shaped to mate with the vertical wall 122 and which includes a radial portion 128 adapted to engage the first contact point 118 and an angled portion 130 adapted to engage the second contact point 120.

As illustrated best in FIGS. 2 and 7, a vertically-extending spring clip 132, which is preferably formed as an integral component of a second angled portion 131 of the wall 122 of carousel 18, is adapted to engage an angled side wall of the cartridge 80 opposite the wall 130 and to bias the cartridge 80 in a circumferential direction against the contact points 118 and 120. The spring clip 132 preferably includes the previously described tab 102 as an integral component thereof.

To facilitate the alignment of the cartridge 80 when it is being inserted into an opening 98 on the carousel 18, a second radially-extending wall oppositely disposed to the wall 122 is provided on the carousel 18 and a corresponding mating wall is provided on the reaction cartridge 80.

As best shown in FIG. 6, the cartridge 80 preferably includes a set of ribs 138 which underlie the surface 93 and which provide a gripping surface for an operator to insert the cartridge into or remove the cartridge from the carousel 18.

As best illustrated in FIG. 3, the carousel 18 preferably includes optical positioning means 140. The optical positioning means 140 preferably comprises a parallelepiped structured 142 mounted atop a vertically extending base. Although other shapes could be used for structure 142, the parallelepiped structure is preferred because the edges of such a structure appear to be normal to the arcuate path of motion of the optical reader 32. The base preferably extends vertically from the surface of the carousel 18 a predetermined distance such that the top of the parallelepiped structure 142 is disposed at the same elevation as the surface of a test card 82 when a reaction cartridge 80 is in the locked position in the carousel 18.

The optical positioning means 140 is advantageously used to determine a zero position reference from which the precise position of each test site 84 of each reaction cartridge 80 on the carousel 18 may be computed for precise access by the optical reader 32. In order to precisely determine the positions of the test sites 84 (or any other location on a reaction cartridge), the optical reader arm 35 rotates the optical reader 32 to scan the optical positioning means 140. The optical reader 32 scans the parallelepiped structure in both radial and circumferential directions. On each scan, the optical reader 32 takes a plurality of uniformly spaced optical reflection intensity readings in a manner described in detail below. By comparing the intensity of sequential reflection readings, the precise locations of the edges of the parallelepiped structure are determined. In the preferred embodiment, the locations of the edges are represented as a number of stepper motor counts of the boom arm 30 and the carousel 18 from predetermined home positions. After the edge locations of the parallelepiped structure are determined, the center of the parallelepiped structure 142 is easily derived by dividing the distances between opposite edges by two and adding the result to the number of steps between the home position of the boom arm 30 or carousel 18 and the edge. Knowing the nominal dimension of the carousel 18 and cartridges 80, the position of each test site 84 or other location may then be computed relative to the zero reference coordinates.

As shown in FIG. 4, encoding ring segments 141, which can be read with an opto switch as is hereinafter described in detail, are placed around the carousel 18. The ring segments 141 preferably vary in length to identify each station.

Preferably, the carousel 18 and cartridge 80 are injection molded from a synthetic plastic material. An acetal material is preferred for the carousel 18. A suitable material for the cartridge 80 is commercially available as ABS plastic.

TEST CARD ASSEMBLY

As described above, the preferred reaction cartridge 80 includes a reaction well portion 86 which contains a test card 82 and which is adapted to hold a patient sample and selected reagents in contact with the test card 82 during a test.

Referring to FIG. 8, the test card 82 is preferably a laminate structure comprising a binding layer 83 adhered to a non-absorbent substrate 85 using an adhesive such as a double-sided adhesive film 87. The porous structure of nitrocellulose has been found to have excellent absorption and adsorption qualities for a wide variety of fluid capture reagents which may be used in connection with the invention and is therefore preferred for use. Nylon also possesses similar characteristics and is a suitable binding layer. Preferably, a nitrocellulose binding layer 83 has an average thickness of about 0.005 inches (127 um avg; ranging from approximately 115 to 180 um) and a pore size of about 0.45 um, although some latitude is permissible in these parameters. Preferably, a binding layer 83 is also tested for DNA hybridization capacity to bind proteins or other materials. A nitrocellulose product that has been found to operate well in the preferred embodiment is available from Millipore (Bedford, Mass.) and is designated HAHY nitrocellulose.

The non-absorbent substrate 85 is suitably a polyester film such as MYLAR plastic having a thickness of approximately 0.002 inches. The binding layer 83 is preferably bound to the non-absorbent substrate 85 by a double-sided adhesive film 87 such as the adhesive film designated V-23 or V-29, both of which are commercially available from Flexcon (Spencer, Mass.). An adhesive backed polyester film is commercially available from several sources, including Flexcon. The entire laminate structure comprising the test card 82 is about 0.010–0.014 inches thick.

Rolls of the laminate material (nitrocellulose-adhesive-non-porous backing substrate) preferred for use in the test card 82 of the present invention are made by Millipore (Bedford, Mass.) by combining their nitrocellulose to the adhesive backed film.

In a preferred mode of manufacture of the test cards 82, the rolls of laminate material are cut into sheets (not shown) approximately 5 inches wide by 6 inches long. Each sheet is punched with alignment holes for registration throughout the manufacturing process.

The ultrasound instrument, typically a Branson 4AE or equivalent, includes an ultrasound horn which is configured with a number of raised circular ridges. These ridges, which are preferably raised about 0.025 inches, apply ultrasonic energy when brought into contact with the laminate sheet to create circular or annular depressions 89 (best illustrated in FIG. 8) which go substantially or completely through the binding layer 83 and may enter into the non-absorbent substrate 85 or adhesive film 87. With a transparent substrate, the depressions 89 are substantially optically transparent.

The circular depressions 89 in the binding layer 83 create a plurality of isolated test sites 84 each composed of binding layer material encircled by a moat 99 of air space. Each test site 84 is adapted to support a reaction between a capture reagent and a specific binding component in a test sample and to confine the flow of the capture reagent applied to the test site 84 to a specific isolated area. As shown in FIG. 5, in a preferred embodiment a plurality of test sites 84 isolated by surrounding moats 99 are arranged in a predetermined two-dimensional array on the test card 82. Each test site 84 is preferably approximately 0.1 inches in diameter and each moat 99 is approximately 0.01 inches across. It is preferable, but not essential, to employ an array wherein the moats 99 considerably overlap one another. In this way, the number of test sites 84 on a test card 82 is maximized. In addition, sensitivity may be improved by reducing the amount of unused binding layer material that competes with the test sites for assay binding components.

It is also preferable to have the depression extend substantially through the porous binding layer 83 so that there are few, if any, pores interconnecting adjacent test sites 84 through which the capture reagents might flow. Thus, the depression is substantially through the binding layer and preferably into the adhesive or substrate layer. The depth and character of the depression are controlled by selection of the parameters for the ultrasound instrument. For nitrocellulose, the ultrasound horn total pressure preferably ranges from about 20 psi to 42 psi. The hold time may vary from about 10 ms to about 100 ms; the weld time may range from about 150 ms to about 400 ms; and the horn frequency is preferably approximately 40 kHz.

The two-dimensional array of test sites 84 may be achieved in the presently preferred embodiment by repeated application of an ultrasound horn having an array of six annular ridges. A high precision X-Y positioning table driven by high resolution, computercontrolled stepper motors is used to align the sheet of laminate material under the horn. Advantageously, a single program may be used to control the table movement as well as the horn movement. A plurality of holes are formed in the table and are connected to a vacuum source so that the sheet can be firmly held to the table precisely aligned by placing the alignment holes over locating pins on the table. Following each application of the ultrasound horn, the sheet is moved an incremental amount in the X-axis direction and the Y-axis direction as is appropriate to generate the preferred array shown in FIG. 5. Alternative arrays are completely within the skill of the ordinary artisan in this area.

When a desired number of arrays are welded onto a sheet of the laminate material, the sheet is ready for the addition of one or more selected capture reagents or assay binding components. The terms capture reagent and assay binding component are used interchangeably herein and mean any compound capable of directly or indirectly binding a desired component from a biological test sample. For example, a capture reagent or assay binding component may include antibodies, antigens, biotin, antibiotin, avidin, lectins, or peptide sequence probes, as well as combinations of the above. Typically, reagents are delivered in aqueous solutions, with or without stabilizers, which are discussed in more detail below.

In a presently preferred embodiment, the capture reagent is a specific allergen which binds human IgE class antibodies from a patient serum sample. A fairly comprehensive compilation of such sliergens is found in EP 106324 filed in the name of AXONICS. Of course, it is also possible to employ antibodies as the capture reagent to bind antigens from the patient's sample. Samples can comprise serum, blood, urine, CSF, saliva and the like.

Advantageously, a different capture reagent is delivered to each test site 84 so that a single sample can be simultaneously tested for the presence of binding components specific to each of a panel of different capture reagents. Some test sites 84 may have analyte delivered thereto to serve as positive control sites. Other test sites 84 may have no reagents delivered thereto, and can serve as negative control or reference sites. Preferably, from about 1.5 to 4 ul of capture reagent solution is delivered to each test site 84. This volume exceeds that which can be absorbed or absorbed by the pores of the nitrocellulose comprising each test site 84 and the excess reagent will bead up over the test site 84 until it dries and evaporates. If a significantly greater volume of capture reagent is delivered, however, reagent may fill the moat 99 and cross to adjacent test sites 84, which could result in erroneous test results.

Capture reagent may be delivered to a test site 84 by any number of suitable delivery methods including reagent jetting, metered air pulsing, positive displacement pump, or by capillary tube lowered to the surface of the test site 84. In a preferred mode of manufacture, capture reagents are delivered to a plurality of test sites 84 simultaneously.

Positive displacement is the presently used method of delivering reagents to the test sites 84. In this method, a sheet of test card laminate material is vacuum-mounted on an X-Y positioning table similar to that described previously. A precise volume of reagent (about 2 ul for example) is delivered by a positive displacement syringe pump having a common driving screw or stepper motor which displaces the plungers of a plurality of syringes fixed to a support. The syringes empty through tubing to a plurality of delivery capillary tubes.

Up to 60 (but preferably about 6 to 10) such delivery tubes can be arranged in a fixture which can be raised and lowered using suitable high precision drive means in a first pass to deposit droplets of reagent on the nitrocellulose test sites. The sheet is then moved by the X-Y table and a preselected reagent is deposited on the next array. When all the two-dimensional arrays in a sheet of test card material are filled with the first pass of capture reagents, a new syringe pump set of reagents can be set up for second pass delivery to other test sites in each of the arrays. Offsetting the delivery tubes and the pass routes so that non-adjacent test sites are spotted during each pass and between two passes minimizes the risk of reagents running together prior to drying.

When each test site 84 on a sheet of test card material has been spotted with capture reagents (or control reagents) the test sites are allowed to dry thoroughly at room temperature. Drying time may range from about 3–72 hours, but is most preferably at least 9 hours.

After drying is completed, the binding layer 83 of the test card material is preferably "blocked" with a protein coating such as inactiveted horse serum or fish gelatin. Blocking masks potential non-specific binding sites on the binding layer 83 (including control or reference test sites which have no capture reagent) and eliminates excess unbound capture reagent to reduce competition and non-specific binding. Suitable blocking is obtained during an incubation period of about 1 hour at approximately 37° C. and is preferably accomplished in tanks with agitation during incubation.

Following blocking, the test card material is washed three times in 10 mM Tris buffered saline (TBS) and allowed to dry overnight.

Individual test cards 82 are preferably cut from the dried sheets of laminate material in generally rectangular shapes adapted to fit the reaction wells 86 of the cartridges 80. Registration holes are also used to align the sheets with respect to a punch which operates to cut out the individual test cards 82. In order to optimize assay sensitivity, it is preferred that the cut test cards 82 have minimal unused area of binding layer material.

The individual test cards 82 are preferably adhered to the bottom surfaces of the reaction wells 86 using a two-sided adhesive tape. Precise positioning of the test cards 82 in the wells 86 is critical since accurate optical reading of the test sites 84 depends on precise positioning of the arrays with respect to the zero position reference coordinates described above. For this reason a vacuum jig apparatus (not shown) is preferably used to insert test cards 82 into the wells 86. Each test card 82 is placed in the corner of a jig abutting two sidewalls. Vacuum drawn through holes in the jig holds the test card 82 in place. When the test card 82 is ready for transfer, a movable head aligned with pins on the jig descends over and contacts the test card 82. The vacuum is transferred from the jig to the head and the head, with the test card 82 now attached, is moved to a second jig having identical alignment pins. The head is lowered over the pins and into the reaction well 86 of a cartridge 80 fixed in the second jig so that the head precisely registers the test card 82 in the well 86. The head vacuum is then released and the double-sided adhesive tape on the bottom surface of the well 86 adheres the test card 82 in precise position.

Stabilizers may be used, if desired, to enhance the stability of the capture reagents delivered to the test sites 84. For example, many allergens can be stabilized by cross-linking with known agents. An exemplary listing of such agents and their final preferred concentrations are given in Table 1.

TABLE 1

| Crosslinking Agents | |
|---|---|
| Agent | Concentration |
| 1-ethyl-3-dimethylaminopropyl carbodiimide (EDAC)/NaBH$_4$ | 5 mg/ml/0.4 mg/ml |
| Formalin | 4% |
| Tetrahydrofuran (THF) | 20% |
| Formalin/THF | 4%/20% |
| Acetic acid/NaOH neutralization | 8% acetic acid |
| Glutaraldehyde | 3% |

In addition, some proteins may be stabilized via photo-cross-linking. For example, the use of N-Hydroxysuccinimidyl-4-azidobenzoate (HSAB) and UV light has been described for linking insulin to nitrocellulose. See Kakita et al., *Diabetes* v.31, pp. 648–652, July 1982. Through the use of these known techniques, capture reagent can be fixed to a test site 84 without covalent bonding.

Alternatively, covalent bonding may be used to attach capture reagent to a test site 84, with or without spacer or linker molecules. Functionalization of a binding layer material such as nitrocellulose or nylon can be achieved through a number of mechanisms known in the art.

HORIZONTAL BOOM ARM AND DRIVES

Referring now to FIGS. 9 and 10, a more detailed description of the preferred boom arm 30 is provided. The horizontal boom arm 30 provides means for positioning the optical reader 32 and the wash/waste probe 28 over the cartridges 80 in carousel 18. In a preferred embodiment, the boom arm 30 includes both the probe arm 33 and the optical reader arm 35, mechanically interconnected. Preferably, a high resolution stepper motor 50 is used to rotate the boom arm 30 to position the optical reader 32 and the probe 28 in precise increments along an arcuate path. The stepper motor 50 includes a shaft with a fixedly attached pinion gear 51 which preferably engages a sector gear 52. The sector gear 52 is in turn fixedly mounted to a shaft 53 which supports a fixed end of the optical reader arm 35 of the boom arm 30. The shaft 53 is preferably rotatably mounted to a base plate 54 by conventional bearing means 55. The base plate 54 may be constructed of any suitable material, as for example, cast aluminum.

Since precise alignment between the boom arm 30 and pinion gear is desirable, the boom arm 30 and pinion gear 51 are preferably mounted to their respective shafts by means of a keyed arrangement.

The gear ratio of the sector gear 52 to the pinion gear 51 may be any suitable ratio which provides the precise boom arm positioning required, but a ratio of about 13.88/1 with the pinion gear having a pitch diameter of approximately 0.375 inches and a total of 18 teeth is presently preferred.

The carousel 18 is preferably driven by a similar stepper motor arrangement. A carousel stepper motor 56 mounted to the base plate 54, rotatably drives a shaft with a fixedly attached pinion gear 57. The pinion gear 57 in turn engages a gear 58 which is fixedly connected to the mounting shaft of the carousel 18, which is suitably mounted to the base plate 54 via a conventional bearing arrangement. In a preferred embodiment, the gear 58 has a pitch diameter of approximately 0.375 inches and a gear ratio of approximately 10/1 with respect to the pinion gear 57, which also has a pitch diameter of about 0.375 inches and a total of 18 teeth. As with the boom arm, the shaft of the stepper motor 56 is preferably provided with a keyed arrangement to precisely position the pinion gear 57.

The sector gear 52 and gear 58 may be made of any suitable material, such as aluminum or a plastic material such as an acetal. A material which is commercially available under the trade name DELRIN is presently preferred for use. Similarly, the pinion gears 51 and 57 may be made of any suitable material. Presently it is preferred to machine these gears from a stainless steel. Suitable precision stepper motors may be purchased from several commercial sources. A particularly preferred stepper motor is commercially available from Vexta as Model No. PXC43-03AA.

Since precise positioning of the optical reader 32 with respect to the carousel 18 is critical, the optical reader 32 must be maintained as level with the carousel 18 as possible. Therefore, the shafts which rotate the boom arm 30 and carousel 18 are preferably carefully mounted with a predetermined center to center distance therebetween with very close tolerance. Additionally, both shafts are preferably carefully mounted to maintain precise vertical alignment between their center axes.

If desired, further leveling may be obtained by fixedly mounting a flat positioning cover plate (not shown) on the carousel drive shaft between the gear 58 and the carousel 18. Such a cover plate preferably includes locating pins which engage corresponding apertures in the gear 58 to precisely align the cover plate to the gear 58. The carousel 18 preferably includes means which engage key means on the cover plate to precisely position the carousel on the cover plate. Preferably, means are also provided to secure the carousel 18 to the cover plate. The cover plate may be made of any suitable material such as aluminum coated with a suitable finish.

As mentioned previously, exact positioning of the boom arm 30 and carousel 18 is accomplished by counting the number of steps taken by the stepper motors 50 and 56. In a preferred embodiment, exact positioning of the optical reader 32 over any test site 84 of a cartridge 80 on the carousel 18 is implemented by a combination of movement of the optical reader 32 in an arcuate path and rotation of the carousel 18 to bring a cartridge 80 into a reading position which intersects the path of the optical reader 32.

Since the precise number of steps taken by stepper motors 50 and 56 is critical for positioning the reader head 32 over any particular test site 84, backlash transmitted from the stepper motors 50 and/or 56 to the gears 52 and 58 may introduce positioning errors which may introduce error into the optical readings. In order to reduce such backlash, floating mounting means are preferably provided for the stepper motors 50 and 56. In a particularly preferred embodiment, for example, a spring plate 61 (shown in FIG. 11 with respect to stepper motor 50) is adapted to provide the pinion gear 51 with a degree of freedom of movement in the Y-direction while restricting movement in the X-direction. The spring plate 51 is fixedly mounted to the base plate 54 near the outer section 62. The stepper motor 50 is fixedly attached to the center portion 63 of the spring plate 61 by conventional fastening means. In this manner, the pinion gear 51 firmly engages the sector gear 52 when the stepper motor 50 is rotating in a forward direction. The single direction of freedom of movement provided by the spring plate 51 prevents any backlash from the stepper motor 50 from being transmitted to the sector gear 52.

Referring to FIG. 9, the horizontal probe arm 33 of the boom arm 30 has a fixed end which is mechanically connected to the optical reader arm 35 and a free end which carries the wash/waste probe 28. The probe arm 33 is preferably pivotally mounted to ears extending downwardly from the optical reader arm 35 by a pivot pin 65.

In a preferred embodiment, a linear actuator motor 66 having a shaft 67 is coupled to a tab 68 which extends upwardly from the probe arm 33. When the shaft 67 is retracted, the probe arm 33 pivots upwardly about the pivot pin 65. When the shaft 67 is extended, the probe arm 32 pivots downwardly about the pivot pin 65. Suitable linear actuators motors are commercially available from a number of sources including Airpax.

As best illustrated in FIG. 9, the outward side portion of the probe arm 33 may be left open to allow access to the wash and waste tubing 23 and 21, which may occasionally or routinely need to be replaced. In a preferred embodiment, the probe arm 33 is provided with snap or guide means to hold the tubes 21 and 23 in place and allow easy removal and insertion of the tubing.

The tubes 21 and 23 preferably connect to probe block means 31 which may be mounted proximate the free end of the probe arm 33 in any suitable fashion. The probe block means 31 provides means for both the wash and waste pumps 25 and 27 to deliver and remove fluid through the same wash/waste probe 28. The probe block 31 prevents contamination of the probe 28 by providing separate entry points for wash and waste fluids with the wash point preferably being above the waste point. Both the wash and waste points connect to a common fluid channel which in turn opens into the probe 28. Priming of the probe block means 31 may be accomplished by delivering wash solution to the probe block and aspirating fluid from the probe block simultaneously. As mentioned previously, the waste pump 27 is preferably operated at a greater rate than the wash pump 25 so that during priming the wash solution never escapes the probe tip 28 and is passed directly into the waste system. This priming procedure is preferably performed before each test run and is also advantageously performed after changing wash and waste units 22 and 24 or before and after tubing changes.

Preferably, the drive arrangements also include home position indicator means associated with the carousel 18 and boom arm 30. Such means advantageously provide signals indicating when the carousel 18 and boom arm 30 are in their respective predetermined home or starting positions. These means include optical switches (not shown) which cooperate with optical blocking flags on the carousel 18 and probe arm 30 to indicate when the carousel 18 and probe arm 30 pass through predetermined home positions. The previously described encoding ring segments 141 can serve as home position indicators. Suitable optical switches are commercially available from Opto Switch, Inc. of McKinney, Tex. as Model No. 0288. These switches are particularly preferred for use with a microprocessor-controlled analyzer because of their ability to generate a digital output.

OPTICAL READER

In a presently preferred embodiment, the optical reader 32 operates on a principle of diffuse reflectance to read test results from the test sites 84 of the reaction cartridges 80. In the diffuse reflectance principle of operation, optical radiation is emitted onto the optically diffuse surface of a test site 84 and the intensity of the optical radiation diffusely reflected by the surface is detected. The density varies as a result of color developments by adding conjugate and developing as described in detail hereinafter. The intensity of the diffusely reflected optical radiation is then processed as described in detail below to obtain an optical density value which indicates the magnitude of the binding reaction between a capture reagent or assay binding component bound to the test site 84 and a second binding component of interest in the sample tested which has a specific binding affinity for the first component. It will be appreciated by persons skilled in the art that alternative optical reading apparatus such as a fluorometer, for example, could also be used if desired depending upon the particular assay chemistry employed.

Figure 12:
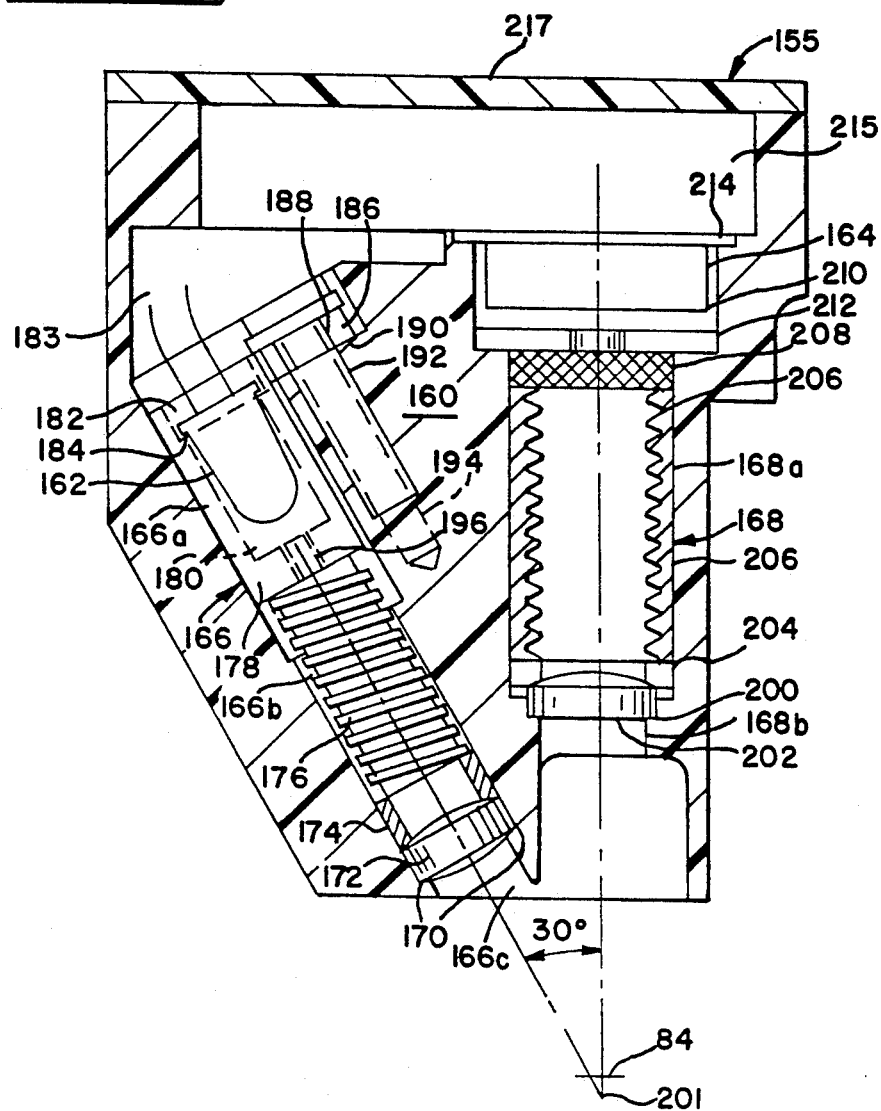
FIG. 12 is a sectional view of the optical reader head of the present invention illustrating a preferred embodiment of an optical reader for reading test results.

Referring to FIG. 12, in the preferred embodiment the optical reader 32 comprises a reflectometer 160 which is mounted in a reader head 155. The readerhead 155 is preferably integrally formed with or, alternatively, mechanically connected to the free end of the horizontal optical reader boom arm 33 as best seen in FIGS. 1 and 9.

In the presently preferred embodiment, reflectometer 160 includes optical source means 162 and optical detector means 164. The optical source means 162 is preferably a solid state device such as a light emitting diode (LED). In particular, a model H-3000 high intensity red LED which is sold commercially by Stanley and which emits optical radiation at a nominal wavelength of approximately 660 nanometers at 35 degrees centigrade is preferred. The optical detector means 164 is also preferably a solid state device such as a photodiode or phototransistor. In particular, a model VDT 020D hybrid silicon photodetector/amplifier which is available commercially from United Detector Technology is preferred.

A cylindrical illumination bore 166 and a cylindrical reflection bore 168 are provided in the optical reader head 155 by means of appropriate machining. The reflection bore 168 is preferably formed vertically so that its center axis is substantially perpendicular to the surfaces of the test sites 84 to be read when the reader 32 is positioned over a reaction cartridge 80. The illumination bore 166 is preferably formed with its center axis being at an acute angle from the vertical center axis of the reflection bore 168. In particular, the illumination bore 166 is preferably formed with its center axis being at an angle of approximately 30 degrees from the vertical center axis of the reflection bore 168. This arrangement minimizes the amount of optical radiation specularly reflected from a test site to the optical detection means 164 and avoids occlusion of the optical beam emitted by the optical source means 162 by the wall 88 of the reaction well 86, which would undesirably reduce signal levels.

The illumination bore 166 has three concentric sections 166a, 166b, and 166c with the upper section 166a having a slightly larger inside diameter than the middle section 166b and the middle section 166b having a slightly larger inside diameter than the lower section 166c. An annular shoulder 170 is formed between the middle and lower sections 166b and 166c. Lens means 172, which is preferably a circular biconvex lens, has a slightly smaller outside diameter than the inside diameter of the middle section 166b. Lens means 172 is mounted in the middle section 166b and is supported therein by the shoulder 170 about its perimeter. An annular ring 174 having an outside diameter slightly smaller than the inside diameter of the middle section 166b and an inner diameter selected to minimize optical interference with the lens means 172 is mounted in the middle section atop the lens means 172. An annular compression spring 176 also having an outside diameter slightly smaller than the inside diameter of the middle section 166b is mounted lengthwise therein atop the annular ring 174 and is supported thereby about its periphery.

The annular spring 176 extends upwardly into the top section 166a and engages the bottom of a cylindrical LED holder 178 which has an outside diameter slightly less than the inside diameter of the top section 166a and which is mounted in the top section 166a. The LED holder 178 contains a cylindrical LED mounting chamber 180. A concentric cylindrical countersink 182 is formed around the top of the chamber 180 to form an annular shoulder 184 therewith. The shoulder 184 is adapted to support the flanged perimeter of an LED 162 which is mounted in the mounting chamber 180. The LED 162 is also preferably adhered in the mounting chamber 180 using a suitable adhesive to prevent movement thereof which could adversely affect the reading of test results. The LED holder 178 is preferably machined of an anodized aluminum and is provided with a blackened inside surface to minimize optical scattering. However, other processes and materials known to persons skilled in the art and having suitable optical qualities may also be used.

A cylindrical volume aperture 196 having a relatively small diameter compared to the diameter of the bore 166 is preferably provided in the bottom wall of the LED holder 178 to communicate the optical radiation emitted by the LED 162 into the illumination bore 166. The volume aperture 196 is preferably concentric with the mounting chamber 180 and the illumination bore 166 and preferably has a longitudinal dimension that is several times greater than the inside diameter thereof, which in a presently preferred embodiment may be approximately 0.025 inches.

The use of the volume aperture 196 is particularly advantageous in minimizing optical aberrations commonly associated with LED's. For example, typical LED's are known to provide non-uniform sources of optical radiation due to the presence of dark spots and/or inaccurate location of the semiconductor junction. The volume aperture 196 operates to collect and diffuse the optical radiation emitted from the lens of the LED 162 to provide a more uniform optical source.

In a presently preferred embodiment, adjustment means are provided for adjusting the optical beam emitted from the illumination bore 166. A mounting tab 186 having an opening 188 is integrally formed with the LED holder 178. The mounting tab 186 mounts in a recess 190 when the LED holder 178 is mounted in the reader head 155. A threaded bore 192 concentric with the opening 188 is provided to engage a threaded fastener 194 such as a screw which may be inserted through the opening 188. The threaded fastener 194 may be manually turned to adjust the location of the LED holder 178 and thus the LED 162 in the illumination bore 166.

The reflection bore 168 has two concentric cylindrical sections 168a and 168b with the inside diameter of section 168a being slightly greater than the inside diameter of section 168b so that an annular shoulder 200 is formed between the two sections. Lens means 202, which is preferably a circular plano-convex lens, has a slightly smaller outside diameter than the inside diameter of section 168a And is mounted therein supported about the periphery of its planar side by the shoulder 200.

An annular compression ring 204 also having an outside diameter slightly smaller than the inside diameter of section 168a is mounted therein atop the lens means 202 and, in particular, atop the convex side of the lens means 202. The inside diameter of the compression ring 204 is preferably dimensioned to minimize optical interference with the lens means 202.

An elongated annular insert 206 having an outside diameter slightly less than the inside diameter of the section 168a and an inside diameter approximately the same as the ring 204 is mounted lengthwise in section 168a atop the annular ring 204. The insert 206 is preferably black and is designed to cover substantially the entire exposed inner surface of the reflection bore 168 in order to minimize optical scattering therein. The inside surface of the insert 206 is advantageously provided with thread-like discontinuities which further assist in this function. In the preferred embodiment, the insert is molded or machined of a black plastic, preferably a plastic sold commercially under the trade name DELRIN, although other materials having suitable optical properties may also be used.

Preferably, a circular optical filter 208 having an outside diameter slightly less than the inside diameter of the section 168a is mounted therein atop the insert 206. The optical filter 208 is preferably a red, Schott glass, band-stop filter which is substantially transmissive only to optical radiation having wavelengths above approximately 630 nanometers.

A cylindrical detector well 210 having an inside diameter greater than the inside diameter of the section 168a and concentric with section 168a is preferably formed around the top of section 168a. An annular aperture element 212 having an outside diameter slightly less than the inside diameter of the detector well 210 is mounted therein overlying the optical filter means 208. The optical detector means 164 extends inside the detector well 210 with its optically active surface facing the aperture element 212. In a preferred embodiment, the optical detector means 164 is mounted directly to a printed circuit board (not shown) which overlies the detector well 210.

The circular aperture formed by the inside diameter of the annular aperture element 212 is preferably concentric with the reflection bore 168 and the detector well 210. The diameter of the aperture determines the size of the area of a test site 84 from which reflected optical radiation is introduced to the optically-active area of the optical detector means 164. Preferably, the aperture is selected to have a diameter slightly larger than that of the optical beam which impinges on the test site to provide a slightly increased depth of field. This feature advantageously reduces the sensitivity of the optical detector output signal to minor variations in vertical distance between various test sites and the optical reader 32. In addition, the diameter of the aperture is preferably selected to allow reflected optical radiation to impinge on substantially the entire optically-sensitive surface of the optical detector means 164 in order to maximize the output signal level of the optical detector means 164.

It is possible that when the optical reader 32 is positioned with the reflection bore 168 over a test site 84 located adjacent to the well wall 88 of a cartridge 80, the wall 88 can occlude the optical beam emitted from the illumination bore 166 and adversely affect the reading of the test site. This possibility can be prevented by offsetting the illumination bore 166 radially from the reflection bore 168 toward the free end of the optical reader arm 33 by a few degrees. For example, in a presently preferred embodiment, assuming a vertical wall 88 dimension of approximately 0.5 inches, a nominal vertical dimension of the bottom of the reader head 155 of approximately 0.48 inches relative to the surface of a test site 84 adjacent to the wall 88, and a nominal angle of 30 degrees between the illumination and reflection bores of the reader, an offset of approximately 10.5 degrees has been found suitable to avoid occlusion of the beam.

In order to minimize output signal variatons with height, the optical reader 32 is preferably configured such that the detection aperature 212 is defocused at the intersection point 201 of the optical axis of the two light paths. For reasons explained below, the preferred target plane of the optical reader 32 lies above the intersection point 201, with the illumination field of the optical beam off-centered toward the illumination side of the optical reader 32.

The collection efficiency of the detector optics is increased by raising the target plane toward the optical reader 32 from the intersection point 201. Given the vertical dimension and the angle Value of the above exemplary arrangement, the best focus of the detector aperature 212 lies approximately 0.240 inches above the intersection point 201. However, as to target plane is raised toward the optical reader 32, the illumination field of the optical beam emitted from the illumination bore 166 moves toward the illumination side of the reader 32, moving the illuminated target away from the area of maximum sensitivity of the detector optics. At some point, as the target plane approaches the optical reader 32, the illumination field falls outside of the detectable area and the detector output signal declines. The point of maximum signal is the area of minimum sensitivy to target height. In the exemplary arrangement given above, the point of maximum signal occurs approximately 0.030 inches above the intersection point 201.

In using the optical reader 32, the threaded fastener 194 is preferably used to adjust the distance between the optical source 162 and the lens means 172 to provide a beam of optical radiation at the intercept of the axes of the illumination and reflection bores 166 and 168 having a diameter of approximately 0.03 inches.

The lens means 202 in the reflection bore 168 collects the optical radiation reflected in a substantially perpendicular direction by the optically diffuse surface of the test site 84 lying beneath the reflection bore 168 and projects it onto the surface of the optical filter means 208, preferably slightly defocused. In a particularly preferred embodiment the aperture element 212 is provided with an inside diameter of approximately 0.095 inches so that optical radiation from an area somewhat larger than the area of the test site impinged upon by the optical beam is transmitted to the optically-sensitive area of the optical detector means 164.

Referring now to FIG. 13, a detailed description of a preferred embodiment of a signal processing and control circuit for the optical reader 32 is provided. Preferred components and component values of the circuit are as illustrated.

It should be noted initially that the preferred circuit may be embodied on a conventional printed circuit board using conventional printed circuit fabrication techniques. In a preferred embodiment, the printed circuit board is shaped to fit within the optical reader arm 35 and may be mounted by conventional fastening means in a cavity 215 which extends into the reader head 155 above the reflectometer 160 (FIG. 12). In this embodiment, the top of the optical reader arm 35 is preferably provided as a removable cover 217 which is secured by screws or the like to provide access to the printed circuit board and the reflectometer 160.

The presently preferred optical reader signal processing and control circuit 225 includes means for converting an analog output signal of the optical detector means 164, which is directly related to the intensity of the optical radiation reflected by a test site 84 or other optical target, to a digital signal for further processing. The preferred circuit also includes means for controlling the drive signal of the LED 162 to control the output intensity thereof. In one preferred embodimen: described in greater detail below, this feature is useful to compensate for variations in output intensity due to temperature variations.

More specifically, in the preferred circuit 225 the analog signal output by the optical detector means 164 is communicated to the signal input VIN of A-D converter means 220. A-D converter means 220 is preferably of the voltage to frequency type but other known types of A-D converters may be used if desired. The A-D converter means 220 samples the instantaneous level of the optical detector analog output signal present at the VIN signal input at a rate determined by clock signal CLK IN. Preferably, the CLK IN signal, which may be provided by a crystal oscillator or other known clock signal generator means, has a nominal frequency of approximately 2 MHz.

The A-D converter means 220 generates output signals on the FOUT signal output comprising a digital pulse train having frequency linearly related to the sampled level of the analog signal at the VIN input.

The FOUT signal output is connected to the trigger or clock signal input TRIG of counter means 222, which is suitably a conventional 16-bit counter. Counter means 222 is controlled by a microprocessor 315 (FIG. 15), which is described in greater detail below, by means of a count enable signal COUNT ENAB and a count reset signal COUNT RESET. The COUNT ENAB signal is provided to the counter enable input ENAB and the COUNT RESET signal is provided to the counter reset input RST of the counter means-222.

In the preferred embodiment, the COUNT ENAB signal is used to define an integration period during which the counter means 222 counts the digital pulses generated by the A-D converter means 220. The COUNT ENAB signal may be generated with a predetermined interval by conventional means such as a monostable multivibrator. However, for additional flexibility, the use of a programmable interval timer (PIT) 344 (FIG. 15) is preferred. Thus, in a preferred embodiment, the PIT 344 is programmed to count down a selected interval by the microprocessor 315 which then sets the COUNT ENAB signal to enable the counter means 222. When the PIT 344 times out, the microprocessor 315 responds by resetting the COUNT ENAB signal to inhibit further counting by the counter means 222. By selecting an integration interval greater than the sample period of the A-D converter means 220, the counter means 222 is operative to integrate the optical detector output signal over time and thereby reduce the effect of spurious high frequency noise components. In a presently preferred embodiment, an integration interval of approximately 25 milliseconds is preferred.

Each integration interval corresponds to an optical reading. Following the completion of an integration interval, the microprocessor 315 reads the final count value on the counter outputs D0–D15. The count value represents the intensity of the optical radiation reflected from the surface of a test site 84 or other optical target integrated over the selected time interval. Prior to initiating each subsequent integration interval, the microprocessor 315 generates the COUNT RESET signal to reset the counter outputs D0–D15.

As mentioned previously, in a presently preferred embodiment a high intensity LED is used as the optical source means 162. In order to prevent variations in the temperature of the LED from causing variations in the LED's output intensity which would adversely affect the accuracy of the optical readings, one preferred embodiment of the circuit 225 includes temperature sensing means 226 and LED drive control means 224 which is responsive thereto. The temperature sensing means 226 is suitably a thermistor or similar device that generates a signal the value of which is related to ambient temperature. Preferably the temperature sensing means 226 is mounted as closely as possible to the LED. Referring to FIG. 12 for example, the temperature sensing means 226 may be mounted in a cavity 183 of the optical reader head 155 immediately behind the LED 162. Although not illustrated in FIG. 13 to avoid duplication, A-D converter means and counter means identical to A-D converter means 220 and counter means 222 are preferably provided to convert the analog signal generated by the temperature sensing means 226 to a digital count value which may be read by the microprocessor 315. The LED drive control means 224 preferably comprises voltage-controlled variable impedance means such as transistor means having a collector connected to the cathode of the LED 162 and an emitter connected to ground. The level of an LED drive control signal LED CONTROL determines the base current of the transistor means which in turn determines the impedance value of the collector-emitter path of the transistor means which is in series with the LED 162. Alternatively, other controllable variable level impedance devices could be used.

Figure 15:
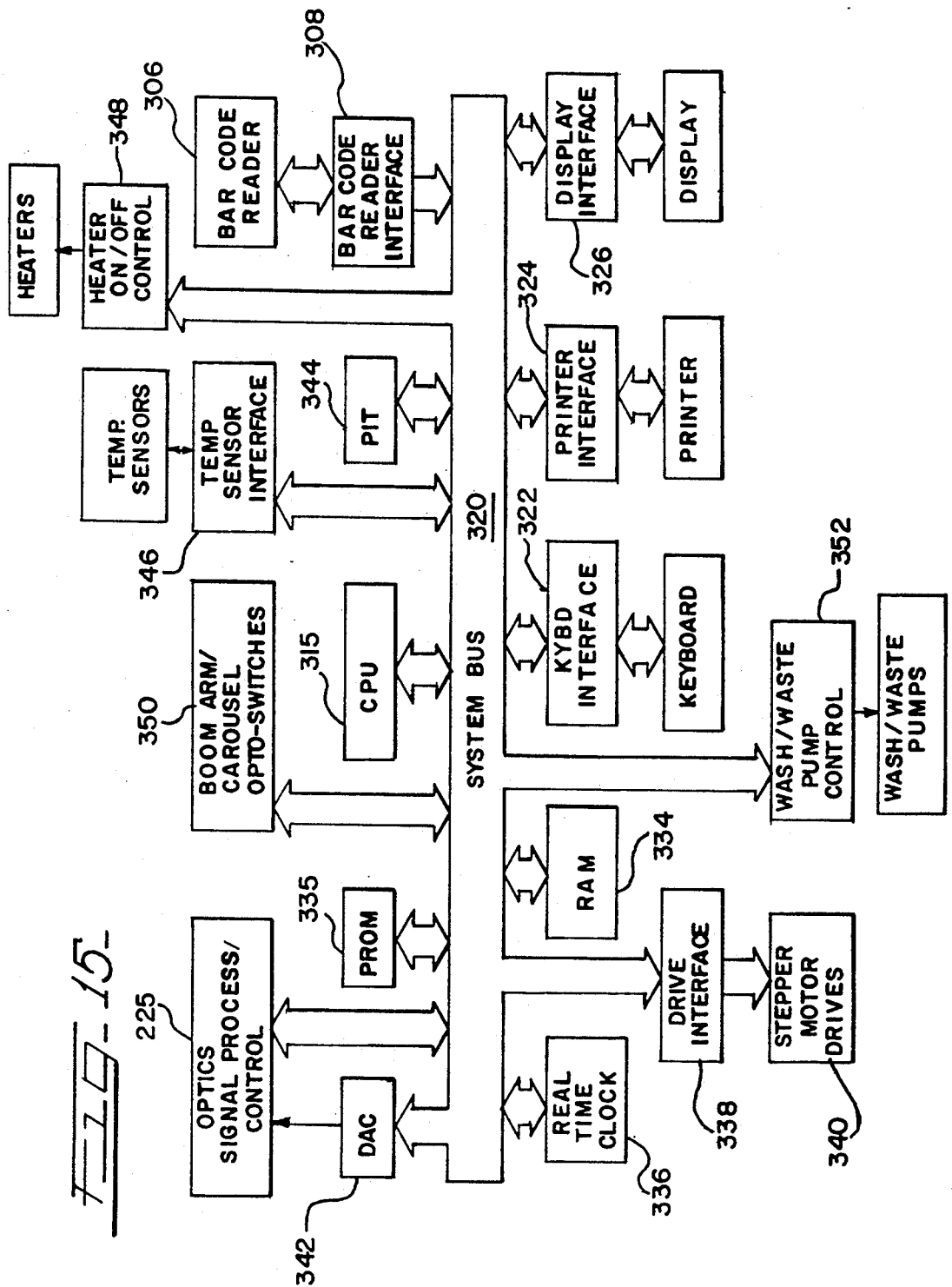
FIG. 15 is a block diagram illustrating a preferred system control architecture of the present invention.

In this embodiment, prior to initiating each integration interval and taking an optical reading, the microprocessor 315 reads the digital value representing the temperature of the LED. A table of digital input values for a D-A converter 342 (FIG. 15) which correspond to LED analog drive currents necessary to maintain the output intensity of the LED at a predetermined constant level at various temperatures is predetermined empirically and stored in a memory such as RAM 334 (FIG. 15). The microprocessor 315 uses the measured digital temperature value as an index into the table, retrieves the appropriate digital D-A input value, and applies it to the D-A converter 342. The D-A converter 342 in turn generates a corresponding analog LED drive control signal LED CONTROL which is applied to the LED drive control means 224. The LED drive control means 224 responds to the LED CONTROL signal to control the drive current allowed to flow through the LED and thereby maintain the desired output intensity of the LED over a certain temperature range.

In a second and more preferred embodiment, the microprocessor 315 uses a predetermined temperature compensation factor to compensate optically-read reflection intensity values for variations of the measured temperature from a predetermined reference temperature, for example 35 degrees centigrade. In this more preferred approach, the microprocessor 315 applies a predetermined digital value which corresponds to a desired output intensity of the LED 162 to D-A converter 342. Although the DAC provides flexibility to change the LED drive current if necessary or desired by simply varying the digital input value, it is not necessary to change the value with changes in temperature because the reflection intensity readings are compensated directly for the temperature changes.

Before describing in detail how the temperature compensation factor used in the more preferred embodiment is computed, attention is directed to FIG. 10 wherein optical reference means 70 is illustrated. Optical reference means 70 provides a white optical reference which is used as a common standard against which to normalize the reflection intensity readings taken from the test sites 84 on the various reaction cartridges 80. Preferably, the optical reference means 70 comprises a punched steel post having a flat top. A ceramic mixture having a preselected optical "whiteness" value is preferably applied to the top of the post and is then baked on. For example, a white ceramic top matching the National Bureau of Standards no. 1 white reference swatch is presently preferred for use. However, it should be noted that the ceramic defines an arbitrarily selected white reference value and that other white standards may therefore also be used. The post is preferably mounted to the analyzer 10 in a location that intersects the arcuate path of the optical reader 32 so that the reflection bore 168 of the reflectometer 160 can be positioned directly over the ceramic top. The post itself is preferably mounted in such a way as to be vertically adjustable so that the vertical distance between the optical reader 32 and the surface of the ceramic can be adjusted to equal the vertical distance between the reader head 155 and the surface of the test sites 84 on the reaction cartridges 80. For example, the post can be threaded on its lower half and screwed into a corresponding threaded receiving bore in the analyzer 10.

A cover 72 is also preferably mounted to the analyzer 10 and is preferably positioned and shaped to overlay the optical reference means 70. The cover 72 is adapted to prevent dust particles or other debris from accumulating on the ceramic surface of the reference means and changing the optical reflectance of the ceramic surface. The cover 72 is preferably pivotally mounted and biased in a normally closed position. Corresponding tabs (not shown) may be provided on the cover 72 and boom arm 30 so that when the optical reader 32 is rotated into position to read the optical reference means 70, the tabs engage and pivot the cover 72 to expose the ceramic surface. When the boom arm 30 rotates away from the reference means 70, the cover 72 preferably returns to its normally-closed position.

Describing now in detail the preferred process of computing the temperature compensation factor, it is initially noted that it has been empirically determined that the output intensity of the LED 162 in the presently preferred embodiment varies substantially linearly with variations in temperature over an expected maximum temperature range of approximately 30°40° C. Accordingly, a linear equation which relates the LED output intensity to temperature can be derived.

A preferred process of deriving the equation involves first positioning the optical reader 32 over the reference means 70, taking a dark reflection intensity reading with the LED off, and storing the reading. Next the temperature in the processing chamber 11 is cycled through the expected range of temperature values and a plurality of reflection intensity readings are taken of the reference means 70 over the entire temperature range. Each time a reading is taken the temperature is measured. Each reflection intensity reading is netted by subtracting the stored dark reflection intensity reading in order to remove components due to the presence of ambient radiation. The corresponding measured temperature and net reflection intensity data pairs are then stored. This procedure is preferably repeated at least two more times to generate a representative body of data.

Next the corresponding data pairs generated during each temperature cycle are processed using conventional linear regression techniques to obtain the slopes and intercepts of the best fit linear equations which define a predicted relationship between the reflection intensity of the known white reference means 70 and measured temperature for each cycle. Each derived equation is then solved to obtain a net reflection intensity value at 35 degrees centigrade and the slope value of each equation is normalized to 35 degrees by dividing the slope value by the predicted net intensity value at 35 degrees. The normalized slope values are then averaged and the average slope value, which is expressed in units of counts per degree, is stored as the temperature compensation factor.

In a third and even more preferred embodiment, the thermistor 226 of the first embodiment is replaced by a second optical detector (not shown). In this embodiment, the second optical detector is mounted directly behind the LED 162 and generates an analog signal having magnitude directly related to the intensity of the optical radiation back scattered from the LED 162. Each time an optical reading is taken, the signal from the first and second optical detectors are simultaneously converted and integrated over the same integration interval. Then the microprocessor processes the two count values to form the ratio of the measured reflection intensity to the back scatter intensity and thereafter treats the ratio as the reflection intensity reading. Since both readings are equally affected by LED 162 temperature variations, the ratio remains constant and provides a temperature-compensated reflection intensity value. No temperature measurements nor additional compensation of the reflection intensity readings is necessary in this embodiment.

The optical reference means 70 also provides a gray scale reflectance reference value, i.e. optical density value, which is advantageously used to calibrate or normalize the gray scale reflectance values which are derived from reflection intensity readings of the various test sites 84 on the various reaction cartridges 80 taken by the optical reader 32. The gray scale reflectance reference value is assigned to the optical reference means 70 by first reading the reflection intensity value of the optical reference means in the manner described in detail above. Next the reflection intensity value of a plurality of optical standards having known gray scale reflectance values is read. For example, a conventional optical filter test card having a plurality of optical filters, each with a different known gray scale reflectance value may be read. A suitable test card having eight optical filters each with a different known gray scale reflectance value is available commercially from Munsell.

Each of the reflection intensity values read from the optical reference means 70 and the optical standards is netted by subtracting the previously stored dark reflection intensity of the optical reference means 70. Then each of the net reflection intensity values is compensated or normalized to 35° C., if necessary, in the manner previously described.

The temperature-compensated net reflection intensity values and the known gray scale reflectance values for the optical standards are then processed using conventional linear regression techniques to define the predicted relationship between the gray scale reflectance value of an optical surface and the corresponding reflection intensity value of the surface measured by the optical reader. The temperature-compensated, net reflection intensity value of the optical reference means 70 is used to solve the linear regression for the predicted gray scale reflectance value of the optical reference means 70. This value is assigned as the gray scale reflectance reference value and is stored for use in normalizing subsequently taken reflection intensity readings of the various test sites 84.

In the presently preferred embodiment, the reflection intensity value read by the optical reader 32 from each test site 84 is converted into a corresponding optical density value. As mentioned previously, the optical density value of a test site 84 may be directly related to the magnitude of the binding reaction between a capture reagent disposed thereon and a corresponding assay binding component of interest in the tested sample which is specific to the capture reagent. This in turn indicates the degree of allergic sensitivity of the patient to the particular binding component, where for example the capture reagent is a preselected allergen and the binding component is a human IgE class antibody specific therefor.

The optical density value determined for each test site 84 may be recorded directly as the result of the assay associated with the site. However, it has been found that different IgE class antibodies, even though having the same concentrations, produce different levels of allergic sensitivity in patients brought into contact with allergens for which the antibodies are specific. Thus, in a preferred embodiment, the optical density values are converted to a five level class score ranging from 0, which represents no allergic sensitivity, to 4, which represents very high allergic sensitivity. The five level scoring system allows test results to be recorded in a uniform format. Each class score preferably corresponds to a predetermined range of optical density values which may however be different for different assays. In order to provide uniformity and to ensure accuracy, the class scores and corresponding ranges of optical density values for each assay are preferably statistically correlated to the results of the same allergy tests using known techniques such as skin prick and/or RAST testing.

CALIBRATION DATA SYSTEM

In addition to the means described above for providing temperature compensation, optical calibration, and conversion of the reflection intensity values, in a preferred embodiment means are included to provide assay calibration data for use in calibrating or normalizing the assay results from various test sites on various reaction cartridges with respect to common predetermined standard values.

The desirability of providing assay calibration data arises from the fact that the allergens or other assay binding components which are bound to individual test sites during the manufacture of the reaction cartridges are necessarily produced in lots of limited volume. Since each lot cannot be prepared with exactly the same concentration of a particular binding component as any other lot of the same binding component, different test sites bound with the same preselected binding component from different lots can produce different assay results for the same sample.

Lot-specific assay calibration data provided for each different lot provides a means for normalizing the assay results associated with individual test sites on a plurality of reaction cartridges with respect to one or more predetermined common standard values. As a result, lot to lot variations do not appear in assay results because all assay results from all test sites are normalized to one or more common standards.

Referring to FIG. 14, in a presently preferred embodiment predetermined assay calibration data 300 is provided, preferably in a machine readable format, for each lot of assay binding components or capture reagents. The assay calibration data 300 may be provided in any suitable format and on any suitable data source media, including for example a magnetic or punched paper tape format and media. An optical bar code format is presently preferred and in particular an optical bar code in a format known in the art as ASCII 3 of 9. Also in the presently preferred embodiment, the assay calibration data 300 is provided on a paper sheet.

The assay calibration data 300 may include both machine readable and human readable information 304 intermixed if desired. The human readable information can be quite useful, for example to assist a technician or other operator in determining which lot and panel of assays the calibration data 300 corresponds to prior to entering the data into the analyzer 10. A corresponding lot number in human readable form is also preferably provided on each reaction cartridge 80 (see FIG. 5) to assist the operator in selecting the appropriate calibration data 300 for each lot before initiating a test cycle.

Alternatively, the assay calibration data 300 may be provided in a human readable format if manual data entry means such as a keypad are available. This is a less preferred alternative because, as will become apparent below, a large amount of calibration data must then be entered manually which increases the hands-on time and expense associated with the tests as well as the risk of error.

The machine readable portion of the calibration data preferably includes at least the calibration data 300 and the lot code which the calibration data 300 corresponds to. If different panels of assays are available on reaction cartridges 80 manufactured using capture reagents from the same lots, a panel identification code is preferably also included as part of the lot code.

It is a significant feature that the calibration data 300 is determined at the time the reaction cartridges are manufactured so that it is unnecessary for a technician or other operator to manually run standards or calibrators prior to initiating a test cycle. The calibration data is preferably generated using a sample from each lot of a capture reagent to assay one or more standard specimens each having a known concentration value of a second assay binding component that is specific for the capture reagent.

As presently preferred, each capture reagent sample is used to assay a number of standard solutions each having a different known concentration value of a sample assay binding component which is specific for the capture reagent. The assay results and the known concentrations of the assayed solutions are processed using conventional least-squares regression techniques to obtain the slope and intercept values for a four point linear calibration curve for each lot of the capture reagent. It will be apparent to persons skilled in the art that more or fewer standard solutions could be assayed depending upon the degree of accuracy required or the nature of the calibration curve.

As mentioned above, it should also now be apparent why manual entry of the calibration data is not preferred. As an example, given a panel of 50 test sites each bound with a different capture reagent, and five standard solutions, 250 individual items of calibration data would have to be manually entered. The number of data items to be entered for a given test cycle would be further multiplied by the number of reaction cartridges manufactured using capture reagents from different lots.

Preferably, conventional optical code reader means 306 and optical code processing means 308 are provided to enter the calibration data 300 for each lot from each sheet 302. More specifically, an optical code processing circuit commercially sold by Hewlett-Packard Co. as model no. HBCR-1800 and any commercially available bar code wand that is compatible therewith may be used. The optical code processing means 308 is preferably interfaced to the microprocessor 315 by any suitable means, for example a conventional peripheral interface adaptor (PIA).

The microprocessor 315 in turn interfaces in a known manner with a data storage means 310 which is suitably a conventional RAM memory such as RAM 334 (FIG. 15). In a presently preferred embodiment, the microprocessor 315 stores the calibration data 300 for each lot in an available area 314 of data storage means 310 reserved for such data and stores the starting storage location together with the lot code and panel code, if any, of the calibration data in a separate lookup table 312 either in data storage means 310 or in other storage means if desired. As shown in FIG. 14, for example, three sets of calibration data, each corresponding to a different lot of capture reagents, are shown stored in data storage means 310 together with the corresponding lot code and starting storage location (in hexadecimal) for each set.

As mentioned previously, code means 94 are preferably provided on each reaction cartridge 80 delivered to the technician or other operator for carrying out a panel of assays. In a preferred embodiment, each code means includes, among other items of information, a code 318 identifying the lot from which the capture reagents bound to the test sites 84 of the cartridge originated. In addition, if multiple cartridges containing different preselected panels of assays and manufactured using capture reagents from the same lot are available, the code 318 also preferably includes a panel identifying code.

For purposes of this feature of the invention, the code means 94 may take any suitable format and may be presented on any suitable data source media. However, it is preferred that the code means 94 be machine readable and in particular it is preferred that the code means 94 be in an optical bar code format. In addition, although the code means is preferably applied to the reaction cartridges 80 in the presently preferred embodiment, it is understood that the code means could be applied to other means used for carrying out assays in different arrangements. Without limitation, other means could include various fluid containers, reaction containers or cartridges, solid-phase test substrates, or the like.

In operation, prior to initiating a test cycle, the operator preferably inspects the reaction cartridges to be used and notes the lot numbers. The operator then obtains the calibration data sheets 302 having the corresponding lot numbers and uses the optical code reader means 306 to enter the calibration data from the sheets into the analyzer 10 where it is stored as described above.

During operation of the subsequent test cycle, the analyzer 10 preferably uses a second optical code reader 316 to read the code means 94 on each reaction cartridge 80 automatically. Suitable optical code readers are available commercially from numerous sources. Alternatively, the optical reader means 32 could be used to read the code means 94 if desired. Less preferably, the code means 94 can be read manually from each cartridge 80 using the optical code reader means 306 or other manually-manipulated code reader means or entered manually using the keypad.

The microprocessor 315 stores the lot and panel code, if present, entered from each cartridge 80 together with the location of the cartridge 80 on the carousel 18 in a memory 334. At the end of the test cycle when the optical reader 32 reads the assay results from the test sites 84 on each cartridge 80, the microprocessor 315 retrieves the lot code for each cartridge 80 and compares it with the lot codes previously stored in the table 312. When a match is found, the microprocessor 315 uses the corresponding starting storage location in the table 312 to retrieve the actual calibration data 300 from the storage area 314. The microprocessor 315 then uses the calibration data 300 to normalize the assay result for each test site 84, which is determined in the manner previously described, using a regression analysis technique in a manner well known to those skilled in the art. Of course, other known normalization techniques may be used instead if desired.

SYSTEM CONTROL ARCHITECTURE

Preferably, central control means are provided to control the various mechanical and electrical elements of the analyzer 10 in a predetermined manner to perform various preselected panels of assays simultaneously on a plurality of biological samples. The heart of the central control means is preferably a programmable microprocessor 315 which has peripheral control, computational, and data processing capabilities. An Intel 80186 microprocessor has been found to possess the desired capabilities and is presently preferred for use as the central control means.

The microprocessor 315 communicates with and controls the various mechanical and electrical elements of the analyzer 10 by way of its system bus 320. The system bus 320 suitably comprises a conventional computer bus having a sufficient number of data, I/O control, and address lines to accommodate the preferred microprocessor 315 and interfaces for the various mechanical and electrical peripherals comprising the analyzer 10. The selection, interfacing, and operation of the system bus is well within the skill of persons of ordinary skill in the art and further detailed description is unnecessary for a complete understanding of the invention.

Program storage means, preferably in the form of PROM 335, is provided to store a control program which contains the instructions necessary for the microprocessor 315 to control the various electrical and mechanical elements of analyzer 10 to automatically carry out assays. The writing of such a program is well within the skill of persons skilled in the art given the sequence of steps necessary for the microprocessor 315 to carry out an exemplary panel of assays as set forth in detail below. PROM 335 may be any commercially available PROM compatible with the system bus 320 and the preferred microprocessor 315 such as Intel 27512 and/or 27010 EPROM's for example.

Additional data storage is preferably provided for system parameters such as test site 84 locations relative to the zero position reference coordinates, assay calibration data, temperature compensation factor, and the like in the form of RAM 334. Suitable RAM is provided by Dallas Semiconductor DS1235 RAM's, for example.

Preferably also interfaced to the system bus 320 are keyboard, printer, and display interfaces 322, 324, and 326 which interface a keypad 328, printer 330, and display 332 respectively to the microprocessor 315. The printer 330 is preferably a compact thermal printer which may be used to print out assay results following completion of a test cycle by the analyzer 10. The printer 330 is suitably any commercially available printer which is compatible with the microprocessor 315 and system bus 320. The printer interface 324 is preferably a conventional centronics parallel printer interface connected directly to a DMA channel of the preferred Intel 80186 microprocessor. Character data to be printed is downloaded directly from the microprocessor memory to the printer interface which in turn generates the appropriate control signals to control the printer mechanism.

The keypad 328, which has been described in general terms previously, is suitably a conventional matrix-switch type of keyboard. A conventional matrix keypad decoder such as a 74C923 decoder IC preferably decodes the location of each depressed key and generates an interrupt to the microprocessor 315 to communicate the identity of the depressed key for processing according to the instructions of the microprocessor control program.

The display 332 is suitably a small LCD type of display which may be used to provide prompts to the operator during a test cycle. The display may be interfaced to the microprocessor 315 in conventional fashion using a display driver, such as a commercially available Hitachi HD44100 driver IC, and a display controller, such as a commercially available Hitachi HD44780 controller IC. Character data to be displayed is transmitted by the microprocessor 315 to the display controller which in turn controls the display driver to generate the appropriate display signals to display the character data.

In a particularly preferred embodiment, all of the program storage, additional storage, microprocessor, and keypad, printer, and display interface means are provided on a single CPU board which is commercially available from Intel Corp. of Santa Clara, Calif.

The stepper motor drives for the carousel 18 and boom arm 30 are each interfaced to the microprocessor 315 by way of an interface 338. Each interface 338 preferably comprises a programmable interface timer (PIT) such as an 8254 type PIT and a programmable logic controller (PLC) such as a GAL16V8 type PLC. In order to cause a stepper motor to move a number of steps, the microprocessor 315 preferably programs the PIT to count down a selected number of counts at a selected frequency. The PLC is responsive to the PIT counts to output the programmed number of step pulses to the stepper motor at the programmed frequency.

The wash and waste pumps are interfaced to the microprocessor 315 through a wash/waste pump control interface 352 which preferably comprises a pair of conventional motor control relays. The microprocessor 315 outputs motor on and off signals to open and close the relays directly and thereby apply power to and remove power from the pump motors.

The temperature sensors and heaters mentioned previously for controlling the temperature in the processing chamber 11 are interfaced to the microprocessor 315 through temperature sensor and heater on/off control interfaces 346 and 348. The temperature sensor interfaces 346 preferably comprise A-D converters, most preferably of the voltage to frequency type, and counters arranged and operated in the same manner as described above with respect to the preferred optical reader signal processing and control circuit 225. In order to read a sensor, the microprocessor 315 programs a PIT 344 to provide an integration period for the counter and enables the counter. When the PIT signals that the programmed integration interval is over, the microprocessor 315 disables the counter, reads the final count value which represents the measured temperature, and resets the counter for the next read.

The heater on/off control interface preferably comprises a heater on/off control relay. Power to the heater is controlled directly by the microprocessor 315 transmitting logic signals to the interface to open and close the relay.

The optical reader signal processing and control circuit 225 and associated DAC 342, the boom arm and carousel optical switches 350, and the optical code reader means 306 and interface 308 have all been described in detail previously in conjunction with the microprocessor 315.

EXEMPLARY MODE OF OPERATION

A detailed step by step description will now be given of a preferred mode of operation of the presently preferred biological sample analyzer 10 in carrying out an exemplary panel of enzyme immuno assays (EIA's) on each of a plurality of biological samples.

When power is first applied to the analyzer 10, the microprocessor control program preferably causes the microprocessor 315 to go through a series of steps preparatory to performing a test cycle. Initially, the microprocessor 315 programs the drive interfaces 338 of the boom arm 30, the probe arm 33 and carousel 18 stepper motors 50, 56 and 66 to position the boom arm 30, probe arm 33 and carousel 18 in their respective home positions. The microprocessor 315 then awaits acknowledgement, in the form of signals from the optical switches 350 associated with the boom arm 30, probe arm 33 and carousel 18, that they have reached their respective home positions.

After the boom arm 30 and carousel are homed, the microprocessor 315 programs the boom arm and carousel drive interfaces 338 to cause the stepper motors 50 and 56 to rotate the boom arm 30 and carousel 18 into positions where the optical reader 32 is adjacent to the optical positioning means 140. The microprocessor 315 next sends an LED CONTROL signal to the optical reader processing and control circuit 225 to turn on the LED 162. The microprocessor 315 then sequentially programs the drive interfaces 338 for the boom arm 30 and carousel 18 to cause the optical reader 32 to first scan the parallelepiped structure of the optical positioning means 140 radially while the carousel 18 remains stationary, and then for the carousel 18 to rotate the parallelepiped structure past the stationary optical reader 32 circumferentially. During the scanning process, the microprocessor 315 initiates a plurality of equally spaced optical readings in the manner previously described and stores each reflection intensity reading in RAM 334. From the stored readings, the microprocessor 315 calculates the coordinates of the center of the paralellepiped structure as the number of counts from home for the carousel and boom arm stepper motors 50 and 56 as described previously and stores the coordinates as the zero-position reference. The microprocessor 315 then waits for the initiation of a test cycle.

All subsequent positioning of the carousel 18 and boom arm 30 to access any particular location on the carousel 18 or a cartridge 80 is preferably accomplished by the microprocessor 315 by programming the drive interfaces 338 with a number of predetermined carousel and boom arm stepper motor steps which correspond to the location of interest. These steps are preferably predetermined and stored in a location table in RAM 334. The location table (not shown) preferably includes predetermined stepper motor count values for positioning the carousel and boom arm at predetermined positions to provide optical access to the code means 94, probe 28 access to the ports 92 of the reaction wells 86 in a fluid access position, and optical access to each of the test sites 84 in a reaction well 86 of a cartridge 80 in a reading position. Preferably, the step values stored in the location table are taken relative to the coordinates of the stored zero position reference. Thus, the actual number of steps for the boom arm or carousel to reach a particular location from the home position is the sum of the zero position reference coordinates and the step values in the location table.

Prior to initiating a test cycle, the operator obtains the appropriate reaction cartridges 80 for the tests to be performed and notes the lot numbers. The operator then obtains the assay calibration data sheet 302 for each lot number and enters the calibration data 300 for each lot using the optical code reader means 306. The microprocessor 315 responds to the optical code reader means 306 in accordance with the control program to store the calibration data 300 and the lot number and starting storage location data pair in RAM 334 as described above.

The operator preferably initiates a test procedure by pressing the RUN key on the keypad 34. In accordance with the control program, the microprocessor 315 responds to the RUN key at this point by programming the drive interfaces 338 to home the boom arm 30 and carousel 18. The microprocessor 315 then transmits a character string to the display interface 326 to prompt the operator on the display 36 to place a reaction cartridge in the carousel opening at the front of the analyzer 10 and enter the patient ID.

In the exemplary enzyme immuno assay being described, the operator preferably introduces approximately 0.5 ml of patient serum and 0.5 ml of a specimen dilution buffer, such as 10% heat inactivated horse serum in 10 mM (TBS) pH7.4, into the reaction well 86 of a cartridge 80 through the port 92. The operator then preferably manually records a patient identification code on the reaction cartridge 80, loads the cartridge 80 into the opening in the carousel 18 and enters the patient identification code on the keypad 34. The microprocessor 315 responds to the entry of the patient identification code on the keypad 34 in accordance with the control program by storing the location of the cartridge on the carousel 18 with the patient identification code in RAM 334.

The microprocessor 315 then waits for the next entry from the keypad 34. The operator preferably depresses either the INDEX key or the RUN key. If the operator depresses the INDEX key, the microprocessor 315 responds by programming the carousel drive interface 338 to cause the carousel stepper motor 56 to rotate the carousel 18 one cartridge position and present the next carousel opening at the front of the analyzer 10. This process is repeated until all cartridges containing samples to be tested have been loaded on the carousel. When, the operator depresses the RUN key, the microprocessor 315 responds in accordance with the control program to initiate execution of the appropriate test procedures for the samples.

The microprocessor 315 first programs the carousel and boom arm drive interfaces 338 with the step coordinates to sequentially position the optical reader 32 adjacent to the code means 94 on each cartridge 80 and then to scan each code means 94. During each scan, the microprocessor 315 operates the optical reader 32 to take a plurality of reflection intensity readings of the code means 94 and stores the readings. Following each scan, the microprocessor 315 processes the stored readings and derives the code means 94 from the contrast between reflection intensity readings taken from light and dark areas of the code. Alternatively, as mentioned previously, the microprocessor 315 may control other conventional optical code reader means to read the code means 94 if desired.

The microprocessor 315 then processes the code means 94 and derives an assay type code therefrom. The microprocessor 315 is preferably responsive to the assay type code in accordance with the control program to subsequently carry out the steps necessary to perform the identified assay within the parameters of a predetermined protocol for the assay. For purposes of the present description, it is assumed that an enzyme immuno assay is to be performed using a sandwich assay format.

The microprocessor also derives the lot code from the code means 94 and stores it in RAM 334 until needed, together with the corresponding patient identification code and carousel position data.

After the code means 94 on each reaction cartridge 80 has been read, the microprocessor 315 in accordance with the assay type code and the control program initiates a timed incubation cycle. In the exemplary EIA being described, the microprocessor 315 programs one or more of the PIT's 344 to time a sample incubation cycle of 16 hours. During the incubation cycle, the microprocessor 315 programs the carousel drive interface 338 to continuously rotate the carousel to provide gentle agitation and promote binding of the IgE class antibodies in each sample which are specific for the capture allergens bound to the test sites 84 of each reaction cartridge 80.

When the incubation cycle times out, the microprocessor 315 preferably initiates a wash procedure in accordance with the assay type code and the control program. The microprocessor 315 programs the boom arm and carousel drive interfaces 338 to position the boom arm in a predetermined fluid access position and to sequentially position each cartridge on the carousel under the probe 28 at the fluid access position. As each cartridge is brought under the probe, the microprocessor 315 programs the drive interface 338 for the linear stepper motor 66 to pivot the probe 28 downwardly through the port 92 and into the reaction well 86. The microprocessor 315 then transmits signals to the wash/waste pump control interface 352 to sequentially cause the waste pump 27 to aspirate the serum sample from the reaction well 86, the wash pump 25 to introduce a volume of wash fluid into the reaction well 86, the carousel 18 to rotate for a predetermined time, and the waste pump 27 to aspirate the spent wash fluid from the well 86. The microprocessor preferably repeats the steps of introducing, rotating and aspirating wash fluid about three times. The microprocessor then programs the drive interface 338 to cause the linear stepper motor 66 to pivot the probe 28 upwardly out of the reaction well. When the reaction wells 86 of all cartridges 80 have been washed, the microprocessor programs the drive interface 338 to home the boom arm.

The microprocessor 315 next transmits a prompt string to the display interface 326 to prompt the operator to introduce conjugate reagent to the reaction cartridges 80. In the exemplary EiA being described, the analytes or sample binding components of interest in the samples are human IgE class antibodies and the conjugate is preferably goat immunoglobulin which is specific for the epsilon chain of human IgE class antibody conjugated to an enzyme such as alkaline phosphatase or horse radish peroxide (HRPO) conjugate. However as is known in the art, the specific detecting conjugate employed may be varied as long as a detectable label (enzymatic or fluorogenic, for example) is linked to a species (antibody or other identifiable binding agent, for example) capable of detecting the analyte of interest or the analyte-capture reagent complex. It is conceivable to utilize co Ibidal conjugates such as gold or other metal as the detectable label.

The operator introduces the conjugate to the reaction well 86 of the cartridge 80 at the front of the carousel, preferably through the port 16 in the processing chamber door 12, then depresses the INDEX key. The microprocessor 315 responds by programming the drive interface 338 to index the carousel 18 by one position. This procedure repeats until the operator has introduced conjugate to each reaction cartridge 80.

When the conjugate introduction procedure is completed, the microprocessor 315, in accordance with the assay type code and the control program, initiates another timed incubation cycle in the same manner as described above. In the case of the exemplary EIA being described, the conjugate incubation period is preferably approximately four (4) hours. During the conjugate incubation period, the microprocessor 315 also causes the carousel stepper motor 56 to continuously rotate the carousel 18 to provide gentle agitation and promote binding of the conjugate to the anti-body capture reagent-test card complex.

When the conjugate incubation cycle times out, the microprocessor initiates a second wash procedure in substantially the same manner as the first wash procedure. Following the wash procedure, the microprocessor causes the operator to be prompted to introduce a substrate reagent. In the case of the exemplary EIA being described, for an HRPO enzyme label, a preferred substrate is 4-chloro-1-naphthol in isopropanal and hydrogen peroxide. For an alkaline phosphate label, a preferred substrate is 5-bromo-4-chloro-3 indolyl phosphate/Nitro blue tetrazolium (BCIP/NTT) in aminomethyl-propanal. In both cases, the substrate is selected to be acted upon by the enzymatic label of the conjugate to develop a color on the surface of each test site 84 having bound the specific analyte of interest. The colored test site has an optical density related to the magnitude of the binding reaction between the allergen bound to the test site and the sample analyte specific for the allergen. The optical density can be determined from the reflection intensity of the test site read by the optical reader 32 to obtain the degree of allergic sensitivity of the patient to the capture allergen.

The microprocessor preferably operates in accordance with the control program to index the carousel 18 and prompt for introduction of the substrate into each reaction cartridge 80 in the same manner as described above with respect to the conjugate. Following the substrate introduction procedure, in the exemplary EIA, the microprocessor initiates a timed substrate incubation cycle during which the substrate is allowed to remain in contact with the test sites 84 of each reaction cartridge for approximately thirty minutes. During this period, the microprocessor causes the carousel to rotate continuously to provide gentle agitation in the same manner as described above.

Following the substrate incubation period and wash, the microprocessor, operating in accordance with the control program, initiates a drying procedure. Initially, the microprocessor causes the carousel 18 to be rotated to its home position. The microprocessor then causes the display to prompt the operator to remove the cover 90 from the reaction cartridge 80 in the front position of the carousel. The operator preferably opens the door 12 of the analyzer 10 and removes each cover 90 as prompted by peeling it off the top of the reaction well wall 88. The cover 90 may then be discarded. The microprocessor waits for the operator to depress the INDEX key. When the operator depresses the INDEX key, the microprocessor causes the carousel to be rotated by one opening so that the next cartridge 80 is presented at the front position. The microprocessor causes the display to again prompt the operator to remove the cover 92 of the cartridge in the front position. This procedure repeats until the operator removes the covers from all of the cartridges 80 on the carousel 18.

When the cover is removed from the last cartridge and the operator depresses the RUN key, the microprocessor causes the display to prompt the operator to close the processing chamber door 12 and depress the RUN key again. When the operator depresses the RUN key, the microprocessor responds in accordance with the control program to program a timed drying interval of preferably approximately fifteen (15) minutes and to cause the carousel stepper motor 56 to rotate the carousel continuously during the timed interval to promote drying of the test cards 82 in each of the cartridges 80. Also at this time, the dark reflection intensity is first determined with the LED off; then the LED is energized and warms up during the drying cycle.

When the drying interval times out, the microprocessor, in accordance with the control program, automatically initiates a reading procedure, beginning with a reading of the optical reference means 70. The microprocessor sequentially programs the carousel and boom arm driver interfaces 338 to sequentially position each reaction cartridge 80 on the carousel 18 in a predetermined reading position which intersects the arcuate path of motion of the optical reader 32. Once a reaction cartridge 80 is in the reading position, the microprocessor sequentially retrieves the step coordinates for each test site 84 from the location table and causes the carousel and boom arm stepper motors to sequentially position the carousel and boom arm to read each test site 84 in the manner described previously in detail. The microprocessor nets the reflection intensity reading for each test site, temperature compensates it if necessary, and stores it in RAM 334 with the carousel position and patient identification code of the cartridge 80.

When each test site 84 of each reaction cartridge 80 has been read, the microprocessor retrieves the readings for each cartridge 80 from RAM, converts them to an optical density, calibrates them using the stored assay calibration data, and then converts them to a class score all in the manner described previously, and stores them back in DMA accessible memory. When all of the readings have been calibrated and converted, the microprocessor initiates a DMA transfer of the stored test results to the printer interface 324 which in turn causes the printer to print the test results for each patient identification code in the form of normalized class scores for each capture allergen of the panel of assays.

After the test results are finished printing, the microprocessor transmits a prompt string to the display interface 326 to prompt the operator to remove the used cartridges 80 from the carousel 18. The microprocessor controls the indexing of the carousel and the removal of the spent cartridges in substantially the same manner as the introduction of the various reagents described above.

The foregoing description of the preferred embodiments of the present invention has been presented for purposes of illustration and description. It is not intended to limit the scope of the invention, which is defined by appended claims and their equivalents. Various modifications and variations of the preferred embodiments are possible in light of the above teachings and will be apparent to persons skilled in the art. Such modifications and variations do not depart from the spirit or scope of the invention and it is therefore intended that the scope of the invention be defined by the following claims, including all equivalents.

I claim:

1. A rotatable carousel for use in an automated biological assay apparatus which sequentially presents a number of test sites to examination by an optical reader, said carousel comprising a plurality of openings, each having means to receive and hold a reaction cartridge such that each reaction cartridge so held can be brought to precisely the same position for scanning by the optical reader through rotation of said carousel, said receiving and holding means comprising resilient members which bias the reaction cartridge against horizontal, radial and circumferential contact points in response to the insertion of the reaction cartridge wherein each of the openings is bounded by a flat vertical wall having a circumferential portion as the radial contact point and tab means integral with the flat vertical wall which extend into the opening as the vertical contact points and at least one of the resilient members is a spring clip positioned in the bottom of each of the openings having an angled face which is configured to interact with a vertical rib on an inserted reaction cartridge to bias the inserted cartridge against the vertical and radial contact points.

2. The rotatable carousel of claim 1, wherein the flat vertical wall includes radially extending portions one of which includes a spring clip configured to interact with a vertical wall of an inserted reaction cartridge to bias the inserted reaction cartridge against the circumferential contact points.

3. The carousel of claim 2 wherein the circumferential contact points are projections which extend into said openings in a circumferentially direction form another radially extending portion of the flat vertical wall.

4. The carousel of claim 1 wherein the receiving and holding means of each opening include three vertical contact points.

5. The carousel of claim 4 wherein the vertical contact points for each opening which is loaded with a reaction cartridge lie in a common plane with all the vertical contact points of all the other openings loaded with reaction cartridges.

6. The carousel of claim 1 wherein the openings radiate from a common center about which the carousel may be rotated and wherein the circumferential contact points for each opening are so spaced from the circumferential contact points of the other openings that a rotation of a certain number of degrees or an integer multiple of that number will move any reaction cartridge loaded in an opening into precisely the same circumferential position as was previously occupied by a reaction cartridge loaded in another opening.

7. The carousel of claim 6 wherein the radial contact points are so spaced that all reaction cartridges loaded in the carousel are the same radial distance from the common center.

8. An apparatus for use in a biological sample analyzer comprising:
an optical reading head configured to read reflective light absorption positioned above a rotatable cartridge conveying means;
rotatable cartridge conveying means having a plurality of openings each configured to receive a reaction cartridge;
a plurality of reaction cartridges each comprising a solid reaction well capable of stably retaining a fluid for an extended period comprising a sidewall integrally formed with a bottom wall and a support means which lies on the bottom wall and has an array of isolated biological test sites in close proximity to one another which lie in a common plane with each site carrying an immobilized biological reactant and all the sites positioned to be in contact with any fluid retained in said well, said well arranged to provide direct optical access to said array of test sites for reading by an optical reader; and
lock means provided with each of said openings for positioning and locking a said reaction cartridge in a predetermined three-dimensional position in said openings, said lock means comprising resilient members which bias the reaction cartridge against vertical, radial and circumferential contact points such that each cartridge may be brought to precisely the same spatial relationship with the optical reading head upon appropriate rotation of the conveying means.

9. The apparatus of claim 8 wherein said lock means operates automatically in response to the insertion of a reaction cartridge.

10. The apparatus of claim 9 wherein said cartridge conveying means comprises rotatable carousel means and wherein said resilient members are part of radial lock means for positioning and locking said cartridge in a radical direction, circumferential lock means for positioning and locking said cartridge in a circumferential direction, and vertical lock means for positioning and locking said cartridge in a vertical direction.

11. The apparatus of claim 10 wherein said circumferential lock means comprises a radially extending carousel wall having at least one circumferential contact point; circumferential contact point engagement means on said cartridge for engaging said circumferential contact point; and a resilient member for biasing said cartridge such that said circumferential contact point engagement means engages said circumferential contact point.

12. The apparatus of claim 10 wherein said vertical lock means comprises tab means attached to said carousel means for engaging a horizontal surface of said reaction cartridge; and at least one resilient member for biasing said cartridge such that said horizontal surface engages said tab means.

13. The apparatus of claim 10 wherein said radial lock means comprises a circumferentially/extending surface on said carousel, said circumferential surface having at least one circumferential contact point; circumferential contact point engagement means for engaging said circumferential contact point; and at least one resilient member for biasing said cartridge such that said circumferential contact point engages said circumferential contact point engagement means.

14. The apparatus of claim 10 wherein:
said circumferential lock means comprises a radially extending carousel wall having an least one circumferential contact point, circumferential contact point engagement means on said cartridge for engaging said circumferential contact point, and a resilient member for biasing said cartridge such that said circumferential contact point engagement means engages said circumferential contact point;
said vertical lock means comprises, tab means attached to said carousel means for engaging a horizontal surface of said reaction cartridge; and at least one resilient member for biasing said cartridge such that said horizontal surface engages said tab means; and
said radial lock means comprises a circumferentially extending surface on said carousel, said circumferentially extending surface having at least one tangential contact point, tangential contact point engagement means on said cartridge for engaging said tangential contact point, and at least one resilient member for biasing said cartridge such that said tangential contact point engages said tangential contact point engagement means.

15. The apparatus of claim 14 wherein said radially extending carousel wall comprises a flat vetrical wall having at least one circumferential contact point and wherein said circumferential contact point engagement means comprises a flat vertical cartridge wall for engaging said circumferential contact point and wherein said circumferential biasing means includes a spring clip disposed on the radially extending wall of said carousel and a cartridge wall configured to engage said spring clip such that said cartridge is biased in a circumferential direction.

16. The apparatus of claim 14 wherein said tab means includes a plurality of tabs for contacting said horizontal surface at a plurality of points and wherein said means for biasing said cartridge in a vertical direction includes at least one lower spring clip having an angled face and a vertical rib on said cartridge, said rib configured to abut the angled face of said spring clip such that said cartridge is biased in an upward direction.

17. The apparatus of claim 14 wherein said circumferential surface comprises a flat circumferentially disposed vertical carousel wall and said tangential contact point engagement means comprises a flat circumferentially arrange cartridge wall for engaging said circumferentially disposed carousel wall, and wherein said radial biasing means includes at least one spring clip having an angled face and a vertical rib on said cartridge, said rib configured to abut the angled face of said spring clip such that said cartridge is biased in a radially inward direction.

* * * * *

UNITED STATES PATENT AND TRADEMARK OFFICE
CERTIFICATE OF CORRECTION

PATENT NO. : 5,320, 808          Page 1 of 2
DATED     : June 14, 1994
INVENTOR(S) : J.T. HOLEN; E. HICARO, JR.; C.G. PUTTERMAN; T. HUANG; C.W. MERKH It is certified that error appears in the above-indentified patent and that said Letters Patent is hereby corrected as shown below:

Column 3, line 22, change "often" to --ten--.

Column 4, line 53, change "tile" to --the--.

Column 5, line 12, change "in-the" to --in the--.

Column 23, line 31, change "Value" to --value--.

Column 27, line 2, change "30°40°C" to --30°-40°C--.

Column 29, line 41, change "Which" to --which--.

Column 35, line 3, change "(TBS)" to --(TB5)--.

UNITED STATES PATENT AND TRADEMARK OFFICE
CERTIFICATE OF CORRECTION

PATENT NO. : 5,320,808
DATED : June 14, 1994
INVENTOR(S) : J.T. HOLEN, E. HICARO, JR., C.G. PUTTERMAN, T. HUANG
C.W. MERKH It is certified that error appears in the above-indentified patent and that said Letters Patent is hereby corrected as shown below:

Column 36, line 31, change "EiA" to

--EIA--.

Column 36, line 44, change "co Ibidal" to

--coloidal--.

Signed and Sealed this

Sixth Day of December, 1994

Attest:

BRUCE LEHMAN

Attesting Officer  Commissioner of Patents and Trademarks